(12) United States Patent
Lee et al.

(10) Patent No.: US 7,388,014 B2
(45) Date of Patent: Jun. 17, 2008

(54) QUINAZOLINE DERIVATIVES AND THERAPEUTIC USE THEREOF

(75) Inventors: Young B. Lee, Rockville, MD (US); Chang H. Ahn, Potomac, MD (US)

(73) Assignee: Rexahn Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 11/059,376

(22) Filed: Feb. 17, 2005

(65) Prior Publication Data

US 2005/0187231 A1  Aug. 25, 2005

Related U.S. Application Data

(60) Provisional application No. 60/545,487, filed on Feb. 19, 2004.

(51) Int. Cl.
*A61K 31/517* (2006.01)
*A61K 31/519* (2006.01)
*C07D 239/70* (2006.01)
*C07D 239/94* (2006.01)

(52) U.S. Cl. .................. 514/266.4; 514/266.2; 514/266.21; 514/267; 544/251; 544/293

(58) Field of Classification Search ............ 514/266.2, 514/266.21, 266.4, 267; 544/251, 293
See application file for complete search history.

(56) References Cited

U.S. PATENT DOCUMENTS

| | | | |
|---|---|---|---|
| 5,296,484 A | 3/1994 | Coghlan et al. | 514/311 |
| 5,457,105 A | 10/1995 | Baker | 514/234.5 |
| 5,480,883 A * | 1/1996 | Spada et al. | 514/249 |
| 5,710,158 A * | 1/1998 | Myers et al. | 514/266.2 |
| 5,721,237 A | 2/1998 | Myers et al. | 514/266.1 |
| 6,046,206 A * | 4/2000 | Pamukcu et al. | 514/266.21 |
| 6,057,326 A * | 5/2000 | Brasca et al. | 514/266.21 |
| 6,127,541 A | 10/2000 | Onoda et al. | 544/251 |
| 6,258,820 B1 | 7/2001 | Uckun et al. | 514/266.4 |
| 6,645,969 B1 * | 11/2003 | Myers et al. | 514/230.5 |
| 2002/0137757 A1 | 9/2002 | Uckun et al. | 514/260 |
| 2003/0191308 A1 | 10/2003 | Hennequin et al. | 544/60 |

FOREIGN PATENT DOCUMENTS

| | | |
|---|---|---|
| EP | 0 566 226 A | 10/1993 |
| EP | 0 635 507 A | 1/1995 |
| WO | WO 95/19970 A | 7/1995 |
| WO | 96-29331 * | 9/1996 |
| WO | WO 96/29331 A | 9/1996 |
| WO | WO 96/30347 A | 10/1996 |
| WO | WO 96/33978 A | 10/1996 |
| WO | WO 97/30034 A | 8/1997 |
| WO | WO 97/49688 A | 12/1997 |

OTHER PUBLICATIONS

U.S. Appl. No. 08/620,719, filed Mar. 1996, Himmelsbach et al.*

Philip Skehan et al., New Colorimetric Cytotoxicity Assay for Anticancer-Drug Screening, Articles, pp. 1107-1112, vol. 82, No. 13, Jul. 4, 1990.
Alexander J. Bridges et al., Tyrosine Kinase Inhibitors 8. An Unusually Steep Structure-Activity Relationship for Analogues of 4-(3-Bromoanilino)-6, 7-dimethoxyquinazoline (PD 153035), a Potent Inhibitor of the Epidermal Growth Factor Receptor, Journal of Medicinal Chemistry, 1996, vol. 39, No. 1, pp. 267-276, 1996.
Gordon W. Rewcastle et al., Tyrosine Kinase Inhibitors. 9. Synthesis and Evaluation of Fused Tricyclic Quinazoline Analogues as ATP Site Inhibitors of the Tyrosine Kinase Activity of the Epidermal Growth Factor Receptor, Journal of Medicinal Chemistry, 1996, vol. 39, No. 4, pp. 918-928, 1996.
Brian J. Palmer et al., Tyrosine Kinase Inhibitors. 11. Soluble Analogues of Pyrrolo- and Pyrazoloquinazolines as Epidermal Growth Factor Receptor Inhibitors: Synthesis, Biological Evaluation and Modeling of the Mode of Binding, Journal of Medicinal Chemistry, 1997, vol. 40, No. 10, pp. 1519-1529, 1997.
Jeff B. Smaill et al., Tyrosine Kinase Inhibitors 17. Irreversible Inhibitors of the Epidermal Growth Factor Receptor: 4-(Phenylamino) quinazoline- and 4-(Phenylamino) pyrido [3,2-d] pyrimidine-6-acrylamides Bearing Additional Solubilizing Functions, Journal of Medicinal Chemistry, 2000, vol. 43, No. 7, pp. 1380-1397, 2000.
HOU Chemical Abstracts AN 138:117246 (2003).
Denny Chemical Abstract AN 135:313144 (2001).
Denny Chemical Abstract AN 125:25623 (1996).
Bridges Chemical Abstract AN 124:134940 (1995) (Equivalent to C35).
Rewcastle Chemical Abstract AN 125:256632 (1995).
Bigar Chemical Abstract AN 76:34199 (1970).
Lutz Chemical Abstract AN 71:30492 (1968).
Biniecki Chemical Abstract AN 57:83258 (1961).
Szczepankiewicz Chemical Abstract AN 134:147558 (2000).
Szczepankiewicz Chemical Abstract AN 128:244010 (1998).
IFE Chemical Abstract AN 123:285897 (1995).
Gour Chemical Abstract AN 140:87658 (2004).
Gour Chemical Abstract AN 137:363033 (2002).
Gour Chemical Abstract AN 135:147398 (2001).
Grigis Chemical Abstract AN 107:198230 (1986) (Equivalent to C36).

(Continued)

*Primary Examiner*—James O. Wilson
*Assistant Examiner*—Tamthom N Truong
(74) *Attorney, Agent, or Firm*—Venable LLP; Michael A. Gollin; Keith G. Haddaway

(57) ABSTRACT

Quinazoline derivatives represented by the general formula

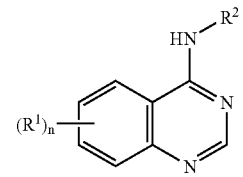

pharmacologically acceptable salts thereof, and compositions containing such compounds are described. Methods for using the compounds for treatment of hyperproliferative disorders are also described.

19 Claims, 1 Drawing Sheet

OTHER PUBLICATIONS

Sun Chemical Abstract AN 97:122727 (1981).
Tobe Chemical Abstract AN 139:46390 (2003).
Calestani Chemical Abstract AN:135:37101 (2001).
Gazit Chemical Abstract AN 125-264991 (1996).
Wakelking Chemical Abstract AN 124:249673 (1996).
Barker Chemical Abstract AN 118:191758 (1992).
Johannsen Chemical Abstract AN 110:75427 (1987).
Csuros Chemical Abstract AN 76:153706 (1972).
Blenke Chemical Abstract AN 139:94784 (2003).
Wright Chemical Abstract AN 134:202418 (2000).
Showalter Chemical Abstract AN 132:87758 (1999).
Bridges Chemical Abstract AN 127:35871 (1997).
Himmelsbach Chemical Abstract AN 126:8131 (1996).
Himmelsbach Chemical Abstract AN 125:275902 (1996).
Alexander J. Bridges, Enantioselective Inhibition of the Epidermal Growth Factor Receptor Tyrosine Kinase by 4-α Phenethylamino) quinazolines, Bioorganic & Medicinal Chemistry, vol. 3 No. 12, pp. 1651-1656, 1995.
Nabih S. Girgis [2], Phosphorus Pentoxide in Organic Synthesis 25, Chemica Scripta 1986, 26, 617-621, Department of Chemistry, Odense University, Campusuej 55, DK-5230 Odense M. Denmark, Received Oct. 24, 1985; accepted Feb. 5, 1986.

* cited by examiner

Fig. 1. RX-0183 causes the inhibition of tumor growth in nude mice sc-injected with HCT116 human colon carcinoma cells.

QUINAZOLINE DERIVATIVES AND THERAPEUTIC USE THEREOF

This application claims priority to U.S. Provisional patent application No. 60/545,487, filed Feb. 19, 2004, which is incorporated herein by reference in its entirety.

FIELD OF THE INVENTION

The invention relates to quinazoline compounds, compositions and their therapeutic methods for the treatment of hyperproliferative disorders, including cancers, by administering quinazoline compounds.

BACKGROUND OF THE INVENTION

Quinazoline compounds are a diverse group with a wide range of physiological effects and activities. Derivatives of 4-aminoquinazoline have been shown to have fungicidal and acaricidal activity (U.S. Pat. No. 3,541,094). Quinazolines bearing a secondary [4-(arylamino)] substituent demonstrate a structure-activity relationship for inhibition of the gastric (H+/K+)-ATPase (Ife et al., J. Med. Chem., 38: 2763-2773 (1995)). Changrolin and related compounds that are quinazoline derivatives can have antiarrhythmic effects (Sun et al., Yao Xue Xue Bao, 16: 564-570 (1981)). Certain quinazoline derivatives have been found to be inhibitors of NF-κB activation and can have an anti-inflammatory effect on carrageenin-induced paw edema in rats (Tobe et al., Bioorg. Med. Chem., 11: 383-391 (2003)).

Some quinazolines have been suggested for the treatment of cell growth and differentiation characterized by activity of the human epidermal growth factor receptor type2 (HER2). See, for example, Myers et. al., U.S. Pat. No. 5,721,237. Some quinazoline derivatives have been suggested for the treatment of specific receptor tyrosine kinase-expressing cancers, especially those expressing epithelial growth factor (EGF) receptor tyrosine kinase. See, for example, Barker, U.S. Pat. No. 5,457,105. While some quinazoline compounds inhibit the growth of brain tumor cells, others with equally potent tyrosine kinase inhibitory activity fail to do so (Narla et. al., Clin. Cancer Res., 4:1405-1414 (1998); Narla et. al., Clin. Cancer Res., 4: 2463-2471 (1998)). Thus, several tumors expressing EGF receptors are not killed by quinazoline compounds, whereas some tumors not expressing EGF receptors are. The cytotoxic activity of quinazoline compounds cannot be attributed to the compound's tyrosine kinase inhibitory activity, and particularly not to the compound's ability to inhibit EGF receptor tyrosine kinase. A chemical structure-activity relationship determining the anti cancer activity of quinazoline derivatives has not been established.

There is a need for novel quinazoline compounds as therapeutic molecules for the treatment of disorders such as cancers. Methods of using both known and novel quinazoline compounds for the treatment of particular disorders are needed.

SUMMARY OF THE INVENTION

Figure 1:
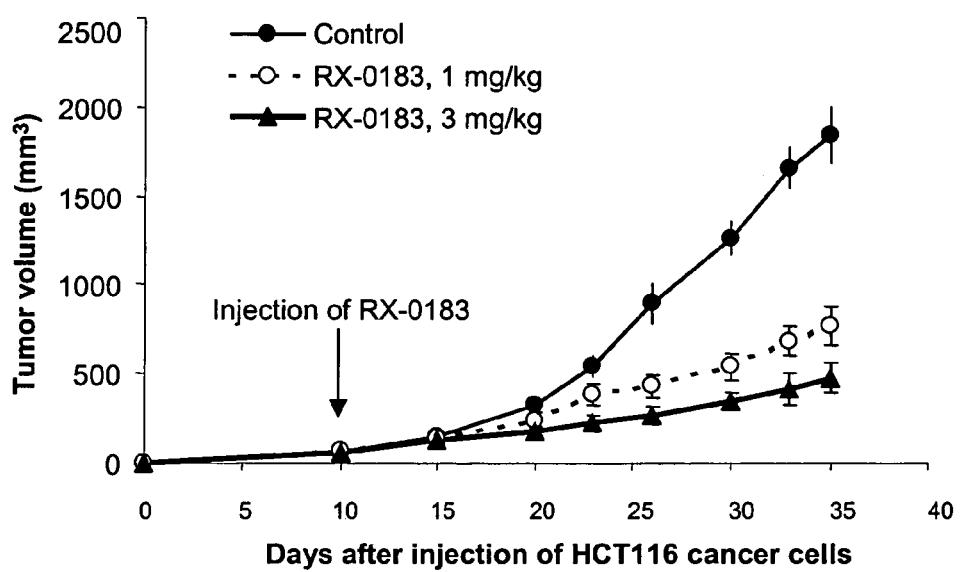
FIG. 1 is a graph showing the inhibition of tumor growth by RX-0183 in nude mice subcutaneously injected with HCT116 human colon carcinoma cells.

Quinazoline compounds were synthesized and analyzed for therapeutic activities, including anti-cancer activities. Quinazoline compounds of the invention are demonstrated as useful for the treatment of hyperproliferative disorders, including tumors, such as breast tumors, brain tumors, and kidney tumors.

DETAILED DESCRIPTION OF THE INVENTION

Definitions

The terms "quinazoline", "quinazoline compound", and "quinazoline derivative" are used interchangeably in this application to mean compounds of formula I, as defined below. All scientific and technical terms used in this application have meanings commonly used in the art unless otherwise specified. As used in this application, the following words or phrases have the meanings specified.

Halo is fluoro, chloro, bromo, or iodo. Alkyl, alkanoyl, etc., denote both straight and branched groups; but reference to an individual radical such as "propyl" embraces only the straight chain radical, a branched chain isomer such as "isopropyl" being specifically referred to. $(C_1-C_4)$alkyl includes methyl, ethyl, propyl, isopropyl, butyl, iso-butyl, and sec-butyl; $(C_1-C_4)$alkoxy includes methoxy, ethoxy, propoxy, isopropoxy, butoxy, iso-butoxy, and sec-butoxy; and $(C_1-C_4)$alkanoyl includes acetyl, propanoyl and butanoyl.

As used herein, "pharmaceutically acceptable carrier" means any material which, when combined with a compound of the invention, allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, in the present invention, the quinazoline derivative is bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

"Treating" means to inhibit, reduce, modulate, ameliorate, or block at least one symptom that characterizes a pathologic condition, in a subject threatened by, or afflicted with, the condition.

A "hyperproliferative disorder" is a disorder characterized by abnormal proliferation of cells, and generically includes skin disorders such as psoriasis as well as benign and malignant tumors of all organ systems. This latter class of hyperproliferative disorders includes, for instance, breast carcinomas (including lobular and duct carcinomas) and other solid tumors, carcinomas, sarcomas, and cancers including carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage.

The present invention comprises quinazoline compounds and their use in the treatment of a hyperproliferative disorder, disease or condition in a subject (e.g., a human patient or other animal subject). Methods according to the invention comprise administering to a subject an effective amount of a quinazoline compound according to the invention. Such a treatment can, e.g., prevent, ameliorate, and/or inhibit symptoms of the hyperproliferative condition, and/or can prevent or inhibit cellular proliferation or growth, for instance in a tumor, such as a malignant neoplasm. A treatment strategy of the invention would decrease the tumor burden, at least to a measurable degree, and improve survival of patients suffering from the hyperproliferative condition. Among the diseases, disorders and conditions susceptible to treatment by agents of the invention are neoplasms, and more specifically tumors of various origins (lung, colon, stomach, smooth muscle, esophagus, non-Hodgkin's lymphoma, non-small cell lung cancer, etc.).

Compounds Usefuil in Methods According to the Inventnion

Compounds useful in methods of the invention include quinazolines having the formula I:

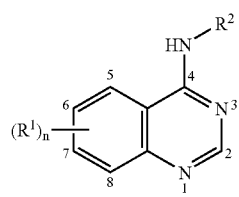

wherein:
 $(R^1)_n$ is selected from 6-NHCH$_2$R$^3$, H, 6-nitro, 6-bromo, 6-iodo, 7-fluoro, 5-methyl, 6,7-dimethoxy, 6,7-diethoxy, imidazol[4,5-g]- and 3-methylimidazol[4,5-g]-; and R$^3$ is selected from the group consisting of —CH(CH$_3$)$_2$, and Ar, where Ar is selected from
  (a) 4-substituted phenyl, wherein the 4-substiuent is selected from —CH(CH$_3$)$_2$, —OCH$_2$Ph, —OCH$_2$CH$_2$CH$_3$, and —Ph;
  (b) 3-substituted phenyl, wherein the 3-substiuent is selected from methoxy, 4-chlorophenoxy, benzyloxy, 4-methoxyphenoxy, 4-methylphenoxy, 3-trifluoromethylphenoxy and methyl;
  (c) 2-substituted phenyl, wherein the 2-substiuent is selected from methyl, nitro, and benzyloxy;
  (d) disubstituted phenyl selected from 2,4-dimethoxyphenyl, 2,6-dimethoxyphenyl, 2,5-dimethoxyphenyl, 3,5-dimethoxyphenyl, 2,5-dimethylphenyl, and 4,4-ethylenedioxy;
  (e) pyridine-3-yl; and
  (f) naphthylen-1-yl, optionally substituted with methoxy in the 2-position;

and wherein
 (i) when $(R^1)_n$ is 6-NHCH$_2$R$^3$, R$^2$ is selected from 3-bromophenyl, 3-chloro-4-fluorphenyl, and
 (ii) when $(R^1)_n$ is H, 6-nitro, 6-bromo, 6-iodo, 7-fluoro, or 5-methyl, R$^2$ is selected from
  (a) cyclohexyl;
  (b) a substituted phenyl, selected from 2,4,6-trimethylphenyl, 2-fluoro-4-chlorophenyl, 4-fluorophenyl and 2-chlorophenyl;
  (c) CH$_2$Ar, wherein Ar is selected from naphthylen-1-yl; 2-trifluoromethylphenyl, and 3-trifluoromethylphenyl;
  (d) (CH$_2$)$_2$Ar, wherein Ar is selected from phenyl, 3-fluorophenyl, and 4-fluorophenyl;
  (e) α-methylbenzyl; and
  (f) 4-phenylbutyl;
 (iii) when $(R^1)_n$ is 6,7-dimethoxy or 6,7-diethoxy, R$^2$ is selected from
  (a) (CH$_2$)$_m$Ar, wherein, m is 1, 2 or 4 and, when m=1, Ar is selected from 2-chlorophenyl, 4-chlorophenyl, 2-fluorophenyl, 2-chloro-6-fluorophenyl, 3-trifluoromethylphenyl, and 3,5-dimethoxyphenyl; when m=2 then Ar is selected from phenyl and 3-fluorophenyl and when m=4, Ar is phenyl; and
  (b) α-methylbenzyl; and
 (iv) when $(R^1)_n$ is imidazol[4,5-g]- and 3-methylimidazol[4,5-g]-, R$^2$ is selected from
  (a) isopropyl;
  (b) 2,4,6-trimethyl phenyl; or phenyl that is optionally substituted in the 2-position with a methyl group or in the 4-position with a substituent selected from methoxy, ethyl, isopropyl, 2,4,6, -trimethyl and n-butyl;
  (c) CH$_2$Ar, wherein Ar is selected from 3-fluorophenyl and 2,5-difluorophenyl;
  (d) (CH$_2$).Ar, wherein m is 2 or 4 and, when m=2, Ar is selected from phenyl, 3-fluorophenyl, 4-methylphenyl and when m=4, Ar is phenyl; and
  (e) α-methylbenzyl.

More particularly, compounds can have the formula II:

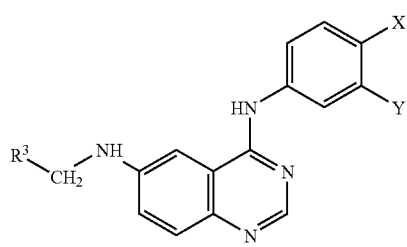

where X=F and Y=Cl or X=H and Y=Br. That is, a compound having either Formula IIa or IIb:

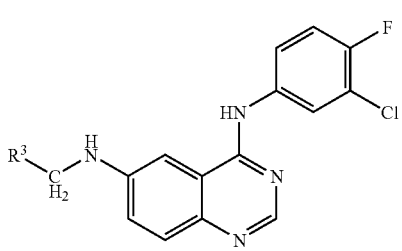

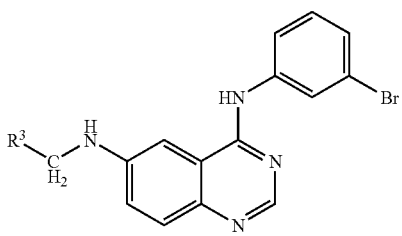

where $R^3$ is isopropyl or is selected from (a) 4-substituted phenyl, wherein the 4-substiuent is selected from —CH(CH$_3$)$_2$, —OCH$_2$Ph, —OCH$_2$CH$_2$CH$_3$, and —Ph; (b) 3-substituted phenyl, wherein the 3-substituent is selected from methoxy, 4-chlorophenoxy, benzyloxy, 4-methoxyphenoxy, 4-methylphenoxy, 3-trifluoromethylphenoxy and methyl; (c) 2-substituted phenyl, wherein the 2-substiuent is selected from methyl, nitro, and benzyloxy; (d) disubstituted phenyl selected from 2,4-dimethoxyphenyl, 2,6-dimethoxyphenyl, 2,5-dimethoxyphenyl, 3,5-dimethoxyphenyl, 2,5-dimethylphenyl, and 4,4-ethylenedioxy; (e) pyridine-3-yl; and (f) naphthylen-1-yl, optionally substituted with methoxy in the 2-position.

Alternatively, the compound can have formula III:

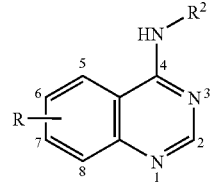

wherein R is selected from H, 6-nitro, 6-bromo, 6-iodo, 7-fluoro, and 5-methyl. That is, a compound having one of Formula IIIa through IIIf:

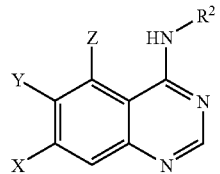

IIIa: X=Y=Z=H
IIIb: X=Z=H; Y=NO$_2$
IIIc: X=Z=H; Y=Br
IIId: X=Z=H; Y=I
IIIe: Y=Z=H; Y=F
IIIf: X=Y=H; Z=CH$_3$ where $R^2$ is selected from (a) cyclohexyl; (b) a substituted phenyl, selected from 2,4,6-trimethylphenyl, 2-fluoro-4-chlorophenyl, 4-fluorophenyl and 2-chlorophenyl; (c) CH$_2$Ar, wherein Ar is selected from naphthylen-1-yl; 2-trifluoromethylphenyl, and 3-trifluoromethylphenyl; (d) (CH$_2$)$_2$Ar, wherein Ar is selected from phenyl, 3-fluorophenyl, and 4-fluorophenyl; (e) α-methylbenzyl; and (f) 4-phenylbutyl.

In yet another embodiment, the compound can have the Formula IV

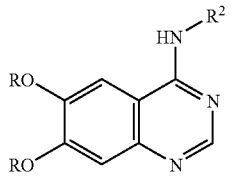

where R is methyl or ethyl. That is, a compound of Formula IVa or IVb:

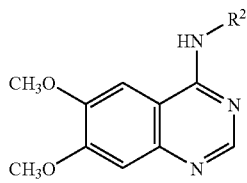

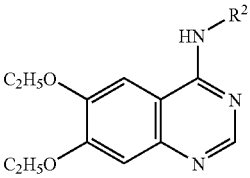

where $R^2$ is selected from (a) (CH$_2$)$_m$Ar, wherein, m=1, 2 or 4 and, when m=1, Ar is selected from 2-chlorophenyl, 4-chlorophenyl, 2-fluorophenyl, 2-chloro-6-fluorophenyl, 3-trifluoromethylphenyl and 3,5-dimethoxyphenyl; when m=2 then Ar is selected from phenyl and 3-fluorophenyl and when m=4, Ar is phenyl; and (b) α-methylbenzyl.

In yet other embodiments, the compounds for use in the method of the invention have the Formula V:

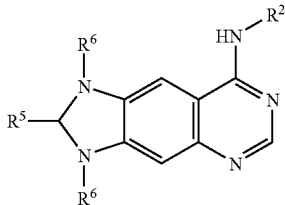

where $R^6$=H, and $R^4$ together with $R^5$ forms a double bond or $R^4$=$CH_3$, and $R^5$ together with $R^6$ forms a double bond. That is a compound having either Formula Va or Vb:

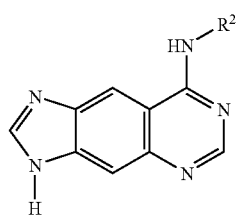

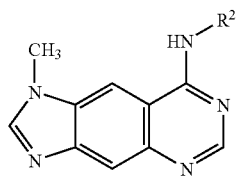

wherein $R^2$ is selected from (a) isopropyl; (b) phenyl, optionally substituted in the 2-position with a methyl group or in the 4-position with a substituent selected from methoxy, ethyl, isopropyl, and n-butyl; (c) 2,4,6, -trimethyl phenyl; (d) $CH_2Ar$, wherein Ar is selected from 3-fluorophenyl and 2,5-difluorophenyl; (e) $(CH_2)_mAr$, wherein m is 2 or 4 and, when m is 2, Ar is selected from phenyl, 3-fluorophenyl, 4-methylphenyl and when m is 4, Ar is phenyl; and (f) α-methylbenzyl.

In some embodiments having the structure of Formula II, $R^3$ is selected from 4-isopropylphenyl, 2-methylphenyl and 2,4-dimethoxyphenyl. In some embodiments having the structure of Formula III, $R^2$ is selected from 2-(3-fluorophenyl)ethyl, 2-phenylethyl, naphthylen-1-ylmethyl, 2-trifluoromethylphenylmethyl, , 2-(4-fluorophenyl)ethyl, 2-fluoro-4-chlorophenyl, 3-trifluoromethylphenylmethyl, cyclohexyl, 2-chlorophenyl, 2,4,6-trimethylphenyl, α-methylbenzyl, and 4-phenylbutyl. In some embodiments having the structure of Formula IV, $R^2$ is selected from 2-chlorophenylmethyl and 2-chloro-6-fluorophenylmethyl. In some embodiments having the structure of Formula V, $R^2$ is selected from isopropyl, 4-phenylbutyl, 3-fluorophenylmethyl, 2-(2-fluorophenyl)ethyl, 2-(3-fluorophenyl)ethyl or phenyl that is optionally substituted in the 4-position with a substituent selected from butyl, isopropyl, ethyl, and methoxy.

In other embodiments, a compound according to the invention has the Formula IIa and $R_3$ is selected from 4-isopropylphenyl and 2,4-dimethoxyphenyl. In yet another embodiment, a compound according to the invention has the Formula IIb, and $R^3$ is 2-methylphenyl. In still other embodiments, a compound according to the invention has the Formula IIIc or IIId and $R^2$ is selected from 2-(3-fluorophenyl)ethyl, 4-phenylbutyl, 2-phenylethyl, naphthylen-1-ylmethyl, 2-trifluoromethylphenylmethyl and 2-fluoro-4-chlorophenyl. In additional embodiments, a compound according to the invention has the Formula IIIb and $R^2$ is 2,4,6-trimethylphenyl. Other embodiments include a compound according to the invention that has the Formula IIIa $R^2$ is selected from 2-(3-fluorophenyl)ethyl, α-methylbenzyl, and 4-phenylbutyl. In other embodiments, a compound according to the invention has the Formula IIIc and $R^2$ is 4-fluorophenyl. Some embodiments have the Formula IIIe or IIIf with $R^2$ being 2-(4-fluorophenyl)ethyl. Some embodiments having Formula IIId have $R^2$ selected from 3-trifluoromethylphenylmethyl, cyclohexyl and 2-chlorophenyl. Certain embodiments include a compound having the formula IVb with $R^2$ selected from 2-chlorophenylmethyl and 2-chloro-6-fluorophenylmethyl. Still other embodiments have the Formula Va and $R^2$ selected from isopropyl, 4-phenylbutyl or phenyl that is optionally substituted in the 4-position with a substituent selected from butyl, isopropyl, ethyl, and methoxy. Additional embodiments of the invention include a compound of Formula Vb where $R^2$ is 2-(3-fluorophenyl)methyl, 2-(2-fluorophenyl)ethyl, 2-(3-fluorophenyl)ethyl, and 4-ethylphenyl.

Exemplary embodiments of the invention include use of a compound of Formula:
  (i) IIb with $R^3$ being 2-methylphenyl;
  (ii) IIIa where $R^2$ is 4-phenylbutyl;
  (iii) IIId in which $R^2$ is 2-phenylethyl;
  (iv) Formula IVb with $R^2$ selected from 2-chlorophenylmethyl and 2-chloro-6-fluorophenylmethyl; or
  (v) Va in which $R^2$ is isopropyl.

In a composition of matter aspect, the present invention includes any of the compounds usefuil in practicing a method according to the present invention which is not previously known. In particular, the present invention specifically excludes compounds wherein
  (a) when $R^2$ is $(CH_2)_2Ph$ or benzyl, $(R^1)_n$ is not H, 6-nitro, 6-bromo, or 6-iodo;
  (b) when $(R^1)_n$ is H, $R_2$ is not $(CH_2)_4Ph$, α-methylbenzyl or 2-chlorophenyl;
  (c) when $(R^1)_n$ is Br, $R^2$ is not α-methylbenzyl;
  (d) when $(R^1)_n$ is 6,7-dimethoxy and $R^2$ is $(CH_2)_mAr$, then
    (i) when m is 1, Ar is not 2-chlorophenyl or 3-trifluoromethylphenyl; and
    (ii) When m is 2, Ar is not phenyl; and
  (e) when $(R^1)_n$ is 6,7-dimethoxy, $R^2$ is not α-methylbenzyl.

Compounds of the invention can be very active against a wide range of hyperproliferatvie diseases, including tumors. For example, compounds according to the invention can be active against tumors of the ovary, tumors of the breast, cervical tumors, tumors of the prostate, tumors of the liver, lung tumors, kidney tumors, colon tumors, pancreatic tumors, brain tumors, stomach tumors and melanoma. By very active, it is meant that a compound can have an $IC_{50}$ of not greater than 10 μM, not greater than 5.0 μM, not greater than 1.0 μM or not greater than 0.5 μM with respect to at least one cell line for a particular tumor. Exemplary cell lines for determining activity include Human OVCAR-3 for tumors of the ovary, MCF-7 or Hs 578T or MDA-MB-231 for breast tumors, HeLa for cervical tumors, PC3 for tumors of the prostate, HepG2 for tumors of the liver, A549 for lung tumors, Caki-1 or UMRC2 for kidney tumors, HT-29 colon tumors, PANC-1 for pancreatic tumors, U251 for brain tumors, MKN-45 for stomach tumors and Lox IMVI for melanoma.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The quinazoline compounds of the invention can be formulated as pharmaceutical compositions and administered to a subject in need of treatment, for example a mammal, such as a human patient, in a variety of forms adapted to the chosen route of administration, for example, orally or parenterally, by intravenous, intramuscular, topical or subcutaneous routes.

Thus, quinazoline compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the quinazoline compounds may be combined with one or more excipients and used in the form of ingestible tablets, buccal tablets, troches, capsules, elixirs, suspensions, syrups, wafers, and the like. The quinazoline compounds may be combined with a fine inert powdered carrier and inhaled by the subject or insufflated. Such compositions and preparations should contain at least 0.1% quinazoline compounds. The percentage of the compositions and preparations may, of course, be varied and may conveniently be between about 2% to about 60% of the weight of a given unit dosage form. The amount of quinazoline compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the quinazoline compounds may be incorporated into sustained-release preparations and devices.

The quinazoline compounds may also be administered intravenously or intraperitoneally by infusion or injection. Solutions of the quinazoline compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the quinazoline compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the quinazoline compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the quinazoline compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or wateralcohol/glycol blends, in which the quinazoline compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the quinazoline compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the quinazoline compounds in a liquid composition, such as a lotion, will be from about 0.1-25% by weight, or from about 0.5-10% by weight. The concentration in a semi-solid or solid composition such as a gel or a powder can be about 0.1-5% by weight, or about 0.5-2.5% by weight.

The amount of the quinazoline compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, 6 to 90 mg/kg/day, or in the range of 15 to 60 mg/kg/day. For example, suitable doses may be 0.5, 5, 10, 25, 50, 100, 250 or 500 mg/kg of body weight per day.

The quinazoline compounds are conveniently administered in unit dosage form; for example, containing 5 to 1000 mg, 10 to 750 mg, or 50 to 500 mg of active ingredient per unit dosage form.

The quinazoline compounds can be administered to achieve peak plasma concentrations of from about 0.5 to about 75 µM, about 1 to 50 µM, or, about 2 to about 30 µM. Exemplary desirable plasma concentrations include at least or no more than 0.25, 0.5, 1, 5, 10, 25, 50, 75, 100 or 200 µM. This may be achieved, for example, by the intravenous injection of a 0.05 to 5% solution of the quinazoline compounds, optionally in saline, or orally administered as a bolus containing about 1-100 mg of the quinazoline compounds. Desirable blood levels may be maintained by continuous infusion to provide about 0.01-5.0 mg/kg/hr, for example at least or no more than 0.005, 0.01, 0.1, 2.5, 5.0 or 10.0 mg/kg/hr. Alternaitively, such levels can be obtained by intermittent infusions containing about 0.4-15 mg/kg, for example at least or no more than 0.25, 0.5, 1.0, 5.0, 10.0, 15.0 or 25.0 mg/kg of the quinazoline compounds.

The quinazoline compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Targeting Quinazolines to Cells

In an exemplary embodiment, the quinazoline compound is targeted to cells where treatment is desired, for example, to human cancer cells. The compound is targeted to the desired cell by conjugation to a targeting moiety that specifically binds the desired cell, thereby directing administration of a conjugated molecule. Useful targeting moieties are ligands which specifically bind cell antigens or cell surface ligands, for example, antibodies against the B cell antigen, CD19 (such as B43) and the like.

To form the conjugates of the invention, targeting moieties are covalently bonded to sites on the quinazoline compound. The targeting moiety, which is often a polypeptide molecule, is bound to compounds of the invention at reactive sites, including $NH_2$, SH, CHO, COOH, and the like. Specific linking agents are used to join the compounds. Linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et al., Bioconjugate Techniques, Academic Press, 1996; Hermanson, et al., Immobilized Affinity Ligand Techniques, Academic Press, 1992; and Pierce Catalog and Handbook, 1996, pp. T155-T201.

EXAMPLES

The invention may be further clarified by reference to the following Examples, which serve to exemplify some of the preferred embodiments, and not to limit the invention in any way.

Examples 1-6

Synthesis of Quinazoline Derivatives

All chemicals were purchased -from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation.

Physical Characteristics

Melting points are uncorrected. $^1$H NMR spectra were recorded using a Bruker 300 MHz spectrometer in DMSO-$d_6$, $CDCl_3$, acetonitrile-$d_3$ or acetone-$d_6$. Chemical shifts are reported in parts per million (ppm) with tetramethylsilane (TMS) as an internal standard at zero ppm. Coupling constants (J) are given in hertz and the abbreviations s, d, t, q, and m refer to singlet, doublet, triplet, quartet and multiplet, respectively. TLC was performed on a precoated silica gel plate (Silica Gel KGF; Whitman Inc). Silica gel (200-400 mesh, Whitman Inc.) was used for all column chromatography separations. All chemicals were reagent grade and were purchased from Aldrich Chemical Company (Milwaukee, Wis.) or Sigma Chemical Company (St. Louis, Mo.).

Example 1

$N^4$-Phenyl, $N^6$- Disubstituted Quinazoline Compounds $N^4$-Phenyl, $N^6$- disubstituted quinazoline derivatives were synthesized and as discussed in Scheme 1. The structures and physical data are shown below:

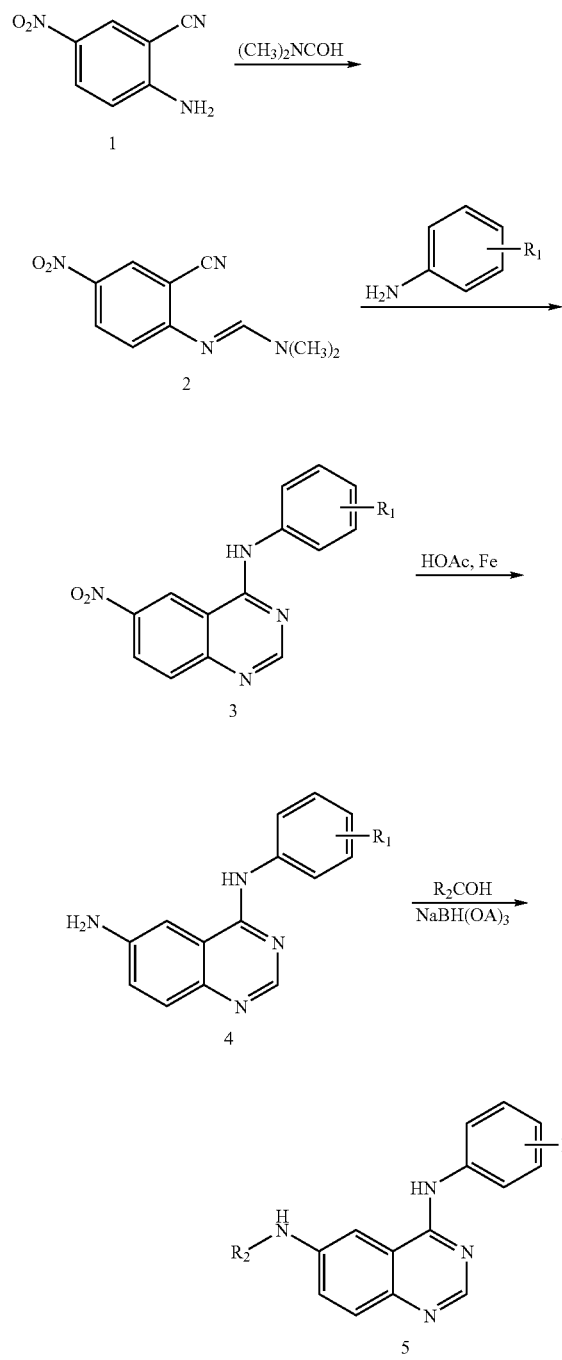

$R_1$ = a: 3-chloro-4-fluoro, b: 3-bromo

TABLE 1

| Compd. No. RX- | R |
|---|---|
| 1057 | naphthalen-1-ylmethyl-NH- |
| 1058 | 4-isopropylbenzyl-NH- |
| 1059 | 2,4-dimethoxybenzyl-NH- |
| 1066 | 4-propoxybenzyl-NH- |
| 1070 | 2-benzyloxybenzyl-NH- |
| 1071 | 3-(3-trifluoromethylphenoxy)benzyl-NH- |
| 1074 | 3-methylbenzyl-NH- |
| 1078 | 2-methoxynaphthalen-1-ylmethyl-NH- |

TABLE 1-continued

Structure: Quinazoline with 4-NH-(3-chloro-4-fluorophenyl) and 6-R substituent

| Compd. No. RX- | R |
|---|---|
| 1082 | —NH—CH₂—(3,5-dimethoxyphenyl) |
| 1083 | —NHCH₂CH(CH₃)₂ |
| 1086 | —NH—CH₂—(3-methoxyphenyl) |
| 1089 | —NH—CH₂—(3-(4-chlorophenoxy)phenyl) |
| 1090 | —NH—CH₂—(pyridin-3-yl) |
| 1092 | —NH—CH₂—(2,6-dimethoxyphenyl) |
| 1093 | —NH—CH₂—(4-benzyloxyphenyl) |
| 1096 | —NH—CH₂—(3-benzyloxyphenyl) |
| 1098 | —NH—CH₂—(3-(4-methoxyphenoxy)phenyl) |
| 1099 | —NH—CH₂—(3-(4-methylphenoxy)phenyl) |
| 1100 | —NH—CH₂—(2,5-dimethylphenyl) |
| 1147 | —NH—CH₂—(2-nitrophenyl) |

TABLE 2

Structure: Quinazoline with 4-NH-(3-bromophenyl) and 6-R substituent

| Compd. No. RX- | R |
|---|---|
| 1010 | —NH—CH₂—(2,5-dimethoxyphenyl) |
| 1025 | —NH—CH₂—(3,5-dimethoxyphenyl) |

TABLE 2-continued

| Compd. No. RX- | R |
|---|---|
| 1140 | —NH—CH₂—(2-benzyloxyphenyl) |
| 1141 | —NH—CH₂—(3-(3-trifluoromethylphenoxy)phenyl) |
| 1142 | —NH—CH₂—(2-methylphenyl) |
| 1143 | —NH—CH₂—(3-methylphenyl) |
| 1144 | —NH—CH₂—(4-biphenyl) |
| 1145 | —NH—CH₂—(2,3-dihydro-1,4-benzodioxin-6-yl) |
| 1146 | —NH—CH₂—(3-(4-chlorophenoxy)phenyl) |

Preparation of N'-(2-cyano-4-nitro-phenyl)-N,N-dimethyl-formamidine (compound 2. —Fifteen grams of 5-nitroanthranilonitrile (compound 1, 92 mmol) was added to 25 ml of N, N-dimethylformamide in 200 ml of chloroform and the reaction mixture was heated under reflux for 5 hrs at 170° C. After cooling the reaction mixture at room temperature for 30 min and at 4° C. for 1 hr, the solid residue was washed with diethyl ether to give 19.23 g of compound 2 (yield, 96%). ¹H-NMR (300 MHz, d₆-DMSO): δ 8.48 (s, 1H), 8.27 (s, 1H), 7.38 (s, 1H), 3.06 (s, 3H), 3.17 (s, 3H).

Preparation of compound 3b—A solution of 10 g of compound 2 (45.82 mmol) and 8.7 g of 3-bromoaniline (50.5 mmol) in 50 ml of acetic acid was heated under reflux for 8 hr at 120° C. After cooling the reaction mixture, the solid residue was washed with diethyl ether to give 11.8 g of compound 3b (yield, 75%). ¹H-NMR (300 MHz, d₆-DMSO): δ 9.67 (s, 1H), 8.79 (s, 1H), 8.58 (s, 1H), 8.20 (s, 1H) 7.98 (d, 2H, J=21 Hz), 7.93 (d, 2H, J=9.0 Hz).

Preparation of compound 4b—A solution of 10 g of compound 3b, 6-nitro-4-(3-bromophenylaniline)quinazoline (28 mmol), 30 ml of acetic acid and 7.8 g of Fe (144 mmol) in 100 ml of ethyl alcohol was heated under reflux for 8 hrs at 120° C. After cooling the reaction mixture, the solid residue was washed with water and ethyl alcohol. The crude solid was purified by $SiO_2$ column chromatography (silica gel; 230-400 mesh) to give 5.5 g of compound 4b (yield, 60%). ¹H-NMR (300 MHz, d₆-DMSO): δ 8.38 (s, 1H), 8.23 (s, 1H), 7.78 (s, 1H), 7.32(s, IH) 7.21 (m, 4H), 5.52 (s, 2H).

Preparation of compound 5b (RX-1010)—Compound 4a, 1.2 eq of 2,5-dimethoxybenzaldehyde and 1.2 eq of sodium triacetoxyborohydride were mixed in dichloromethane and the mixture was stirred for 8 hrs at room temperature. The solvent was removed under reduced pressure and the crude solid was purified by $SiO_2$ column chromatography (silica gel; 230-400 mesh) to give compound 5b. ¹H-NMR (300 MHz, CDCl₃): δ 8.60 (s, 1H), 8.01 (s, 1H), 7.74 (t, 2H, J=8.0 Hz), 7.21 (m, 5H), 6.82 (m, 4H), 4.42 (s, 2H), 3.88 (s, 3H), 3.75 (s, 3H).

Preparation of compound RX-1025—Reaction of compound 4b with 3,5-dimethoxybenzaldehyde as above, preparation of compound 5b, followed by chromatography on $SiO_2$, gave compound RX-1025. ¹H-NMR (300 MHz, d₆-DMSO): δ 8.39 (s, 1H), 8.18 (s, 1H), 7.90 (s, 1H), 7.54 (d, 1H, J=9.0 Hz), 7.36 (m, 4H), 6.64 (s, 2H), 6.38 (s, 1H), 5.7 (s, 1H), 4.37 (s, 2H), 3.71 (s, 6H).

Preparation of compound RX-1057—Reaction of compound 4a with 1-naphthaldehyde as above, preparation of compound 5b, followed by chromatography on $SiO_2$, gave compound RX-1057. ¹H-NMR (300 MHz, CDCl₃): δ 8.42 (s, 1H), 7.86 (m, 3H), 7.54 (m, 7H), 7.07 (t, 1H, J=7.0 Hz), 6.94 (m, 2H), 4.68 (s, 2H).

Preparation of compound RX-1058—Reaction of compound 4a with 4-isopropylbenzaldehyde as above, preparation of compound 5b, followed by chromatography on $SiO_2$, gave compound RX-1058. ¹H-NMR (300 MHz, d₆-DMSO): δ 9.42 (s, 1H), 8.36 (s, 1H), 8.14 (d, 1H, J=3.0 Hz), 7.85 (t, 1H, J=6.0 Hz), 7.53 (d, 1H, J=9.0 Hz), 7.39 (m, 7H), 6.69 (s, 1H), 4.38 (s, 2H), 2.92 (t, 1H, J=6.0 Hz), 1.18 (d, 6H, J=9.0 Hz).

Preparation of compound RX-1059—Reaction of compound 4a with 2,4-dimethoxybenzaldehyde as above, preparation of compound 5b, followed by chromatography on $SiO_2$, gave compound RX-1059. ¹H-NMR (300 MHz, d₆-DMSO): δ 9.45 (s, 1H), 8.36 (s, 1H), 8.14 (d, 1H, J=9.0 Hz), 7.81 (d, 1H, J=6.0 Hz), 7.54 (d, 1H, J=9.0 Hz), 7.43 (m, 2H), 7.27 (s, 1H), 6.96 (t, 2H, J=9.0 Hz), 6.83 (t, 1H, J=8.0 Hz), 6.51 (s, 1H), 4.36 (s, 2H), 3.79 (s, 3H), 3.65 (s, 3H).

Preparation of compound RX-1066—Reaction of compound 4a with 4-propoxybenzaldehyde as above, preparation of compound 5b, followed by chromatography on $SiO_2$, gave compound RX-1066. ¹H-NMR (300 MHz, CDCl₃): δ 8.54 (d, 1H, J=6.0 Hz), 7.87 (t, 1H, J=3.0 Hz), 7.68(d, 1H, J=9.0 Hz), 7.45 (m, 1H), 7.25 (d, 1H, J=9.0 Hz), 7.13 (m, 2H), 6.89 (d, 1H, J=9.0 Hz), 6.75 (s, 1H), 4.19 (s, 2H), 3.91 (t, 2H, J=12.0 Hz), 1.81 (m, 2H), 1.25 (m, 2H), 1.05 (t, 3H, J=9.0 Hz).

Preparation of compound RX-1070— Reaction of compound 4a with 2-benzyloxybenzaldehyde as above, preparation of compound 5b, followed by chromatography on SiO$_2$, gave compound RX-1070. $^1$H-NMR (300 MHz, d$_6$-DMSO): δ 9.45 (s, 1H), 8.36 (s, 1H), 8.12 (d, 1H, J=6.0 Hz), 7.86 (s, 1H), 7.36 (m, 11H), 7.11 (d, 1H, J=9.0 Hz), 6.93 (s, 1H), 6.54 (s, 1H), 5.20 (s, 2H), 4.47 (s, 2H).

Preparation of compound RX-1071—Reaction of compound 4a with 3-[3-(trifluoromethyl)phenoxy]benzaldehyde as above, preparation of compound 5b, followed by chromatography on SiO$_2$, gave compound RX-1071. $^1$H-NMR (300 MHz, CDCl$_3$): δ 8.58 (s, 1H), 7.86 (d, 1H, J=9.0 Hz), 7.72 (d, 1H, J=6.0 Hz), 7.35 (m, 10H), 6.72 (s, 1H), 4.38 (s, 2H).

Preparation of compound RX-1074—Reaction of compound 4a with m-tolualdehyde as above, preparation of compound 5b, followed by chromatography on SiO$_2$, gave compound RX-1074. $^1$H-NMR (300 MHz, d$_6$-DMSO): δ 9.42 (s, 1H), 8.37 (s, 1H), 8.14 (d, 1H, J=6.0 Hz), 7.85 (m, 1H), 7.54 (d, 1H, J=9.0 Hz), 7.28 (m, 6H), 7.15 (s, 1H), 6.72 (s, 1H), 4.39 (d, 2H, J=6.0 Hz), 2.30 (s, 3H).

Preparation of compound RX-1078—Reaction of compound 4a with 2-methoxy-1-naphthaldehyde as above, preparation of compound 5b, followed by chromatography on SiO$_2$, gave compound RX-1078. $^1$H-NMR (300 MHz, CDCl$_3$): δ 8.61 (s, 1H), 7.87 (m, 6H), 7.40 (m, 3H), 7.10 (d, 2H, J=6.0 Hz), 6.91 (s, 1H), 4.61 (s, 2H), 3.97 (s, 3H).

Preparation of compound RX-1082—Reaction of compound 4a with 3,5-dimethoxybenzaldehyde as above, preparation of compound 5b, followed by chromatography on SiO$_2$, gave compound RX-1082. $^1$H-NMR (300 MHz, d$_6$-DMSO): δ 9.41 (s, 1H), 8.37 (s, 1H), 8.16 (s, 1H), 7.95 (m, 1H), 7.37 (m, 4H), 6.64 (t, 1H, J=7.0 Hz), 6.39 (s, 2H), 6.25 (s, 1H), 4.37 (d, 2H, J=12.0 Hz), 3.72 (s, 6H).

Preparation of compound RX-1083—Reaction of compound 4a with isobutyraldehyde as above, preparation of compound 5b, followed by chromatography on SiO$_2$, gave compound RX-1083. $^1$H-NMR (300 MHz, CDCl$_3$): δ 8.58 (s, 1H), 7.90 (t, 1H, J=3.0 Hz), 7.54 (d, 1H, J=6.0 Hz), 7.15 (t, 1H, J=9.0 Hz), 6.70 (t, 2H, J=3.0 Hz), 6.62 (s, 1H), 2.98 (d, 2H, J=6.0 Hz), 2.05 (m, 1H), 1.02 (t, 6H, J=9.0 Hz).

Preparation of compound RX-1086—Reaction of compound 4a with 3-methoxybenzaldehyde as above, preparation of compound 5b, followed by chromatography on SiO$_2$, gave compound RX-1086. $^1$H-NMR (300 MHz, CDCl$_3$): δ 8.58 (s, 1H), 7.88 (d, 1H, J=6.0 Hz), 7.73 (d, 1H, J=9.0 Hz), 7.51 (s, 2H), 7.31 (m, 1H), 7.15 (m, 2H), 6.96 (m, 2H), 6.82 (d, 1H, J=3.0 Hz), 6.70 (s, 1H), 4.37 (s, 2H), 3.80 (s, 3H).

Preparation of compound RX-1089—Reaction of compound 4a with 3-(4-chlorophenoxy)benzaldehyde as above, preparation of compound 5b, followed by chromatography on SiO$_2$, gave compound RX-1089. $^1$H-NMR (300 MHz, CDCl$_3$): δ 8.52 (s, 1H), 7.99 (s, 1H), 7.86 (t, 1H, J=6.0 Hz), 7.66 (m, 2H), 7.26 (m, 3H), 7.12 (m, 3H), 7.07 (s, 1H), 6.90 (m, 3H), 4.33 (s, 2H).

Preparation of compound RX-1090—Reaction of compound 4a with 3-pyridinecarboxaldehyde as above, preparation of compound 5b, followed by chromatography on SiO$_2$, gave compound RX-1090. $^1$H-NMR (300 MHz, d$_6$-DMSO): δ 9.42 (s, 1H), 8.36 (s, 1H), 8.15 (d, 1H, J=3.0 Hz), 7.83 (t, 1H, J=3.0 Hz), 7.52 (d, 1H, J=6.0 Hz), 7.44 (t, 2, J=9.0 Hz), 7.27 (d, 1H, J=9.0 Hz), 7.14 (s, 1H), 6.23 (m 1H), 4.11 (m, 2H).

Preparation of compound RX-1092—Reaction of compound 4a with 2,6-dimethoxybenzaldehyde as above, preparation of compound 5b, followed by chromatography on SiO$_2$, gave compound RX-1092. $^1$H-NMR (300 MHz, d$_6$-DMSO): δ 9.46 (s, 1H), 8.37 (s, 1H), 8.21 (d, 1H, J=6.0 Hz), 7.91 (m. 1H), 7.48 (m, 2H), 7.31 (m, 3H), 6.72 (d, 2H, J=6.0 Hz), 4.28 (s, 2H), 3.85 (s, 6H).

Preparation of compound RX-1093—Reaction of compound 4a with 4-benzyloxybenzaldehyde as above, preparation of compound 5b, followed by chromatography on SiO$_2$, gave compound RX-1093. $^1$H-NMR (300 MHz, d$_6$-DMSO): δ 9.41 (s, 1H), 8.36 (s, 1H), 8.16 (t, 1H, J=6.0 Hz), 7.92 (t, 1H, J=6.0 Hz), 7.55 (d, 2H, J=9.0 Hz), 7.34 (m, 10H), 7.00 (d, 2H, J=6.0 Hz), 6.66 (s, 1H), 5.08 (s, 2H), 4.35 (s, 2H).

Preparation of compound RX-1096—Reaction of compound 4a with 3-benzyloxybenzaldehyde as above, preparation of compound 5b, followed by chromatography on SiO$_2$, gave compound RX-1096. $^1$H-NMR (300 MHz, CDCl$_3$): δ 8.55 (s, 1H), 7.88 (d, 1H, J=6.0 Hz), 7.71 (d, 1H, J=9.0 Hz), 7.35 (m, 9H), 6.98 (m, 2H), 6.66 (m, 3H), 6.65 (s, 1H), 5.05 (s, 2H), 3.33 (s, 2H).

Preparation of compound RX-1098—Reaction of compound 4a with 3-(4-methoxyphenoxy)benzaldehyde as above, preparation of compound 5b, followed by chromatography on SiO$_2$, gave compound RX-1098. $^1$H-NMR (300 MHz, CDCl$_3$): δ 8.58 (s, 1H), 7.93 (d, 1H, J=6.0 Hz), 7.71 (d, 1H, J=9.0 Hz), 7.61 (s, 1H), 7.48 (d, 1H, J=6.0 Hz), 7.26 (m, 2H), 7.15 (m, 2H), 7.02 (d, 1H, J=6.0 Hz), 6.95 (m, 3H), 6.85 (m, 3H), 6.71 (s, 1H), 4.58 (s, 1H), 4.29 (s, 2H), 3.78 (s, 3H).

Preparation of compound RX-1099—Reaction of compound 4a with 3-(methylphenoxy)benzaldehyde as above, preparation of compound 5b, followed by chromatography on SiO$_2$, gave compound RX-1099. $^1$H-NMR (300 MHz, CDCl$_3$): δ 8.55(s, 1H), 7.84 (t, 1H, J=6.0 Hz), 7.68 (d, 1H, J=9.0 Hz), 7.44 (s, 1H), 7.27 (d, 1H, J=6.0 Hz), 7.11 (m, 5H), 6.99 (m, 4H), 6.77 (s, 1H), 4.22 (s, 2H), 2.31 (s, 3H).

Preparation of compound RX-1100—Reaction of compound 4a with 2,5-dimethylbenzaldehyde as above, preparation of compound 5b, followed by chromatography on SiO$_2$, gave compound RX-1100. $^1$H-NMR (300 MHz, CDCl$_3$); δ 8.59 (s, 1H), 7.97 (d, 1H, J=3.0 Hz), 7.74 (d, 1H, J=9.0 Hz), 7.58 (m, 2H), 7.28 (s, 1H), 7.13 (m, 5H), 6.73 (d, 1H, J=3.0 Hz), 4.26 (s, 2H), 2.33 (s, 6H).

Preparation of compound RX-1140—Reaction of compound 4b with 2-benzyloxybenzaldehyde as above, preparation of compound 5b, followed by chromatography on SiO$_2$, gave compound RX-1140. $^1$H-NMR (300 MHz, d$_6$-DMSO): δ 9.42 (s, 1H), 8.38 (s, 1H), 8.15 (s, 1H), 7.86 (d, 1H, J=6.0 Hz), 7.56 (d, 1H, J=9.0 Hz), 7.48 (d, 2H, J=6.0 Hz), 7.32 (m, 9H), 7.11 (d, 2H, J=9.0 Hz), 6.92 (t, 1H, J=6.0 Hz), 6.53 (s, 1H), 5.20 (s, 2H), 4.48 (d, 2H, J=6.0 Hz).

Preparation of compound RX-1141—Reaction of compound 4b with 3-[3-(trifluoromethyl)phenoxy]benzaldehyde as above, preparation of compound 5b, followed by chromatography on SiO$_2$, gave compound RX-1141. $^1$H-NMR (300 MHz, CDCl$_3$): δ 8.50 (s, 1H), 7.98 (s, 1H), 7.62 (m, 2H), 7.35 (m, 3H), 7.13 (m, 5H), 7.04 (s, 2H), 6.94 (d, 1H, J=9.0 Hz), 6.74 (s, 1H), 4.33 (s, 2H).

Preparation of compound RX-1142—Reaction of compound 4b with o-tolualdehyde as above, preparation of compound 5b, followed by chromatography on SiO$_2$, gave compound RX-1142. $^1$H-NMR (300 MHz, CDCl$_3$): δ 8.49 (s, 1H), 8.01 (s, 1H), 7.64 (m, 2H), 7.31 (m, 1H), 7.23 (m, 5H), 7.02 (d, 1H, J=9.0 Hz), 6.77 (s, 1H), 4.27 (s, 2H), 2.38 (s, 3H).

Preparation of compound RX-1143—Reaction of compound 4b with 3-methylbenzaldehyde as above, preparation of compound 5b, followed by chromatography on SiO$_2$, gave compound RX-1143. $^1$H-NMR (300 MHz, d$_6$-DMSO):

δ 9.37 (s, 1H), 8.37 (s, 1H), 8.16 (s, 1H), 7.90 (d, 1H, J=6.0 Hz), 7.54 (d, 1H, J=9.0 Hz), 7.29 (m, 7H), 7.06 (s, 1H), 6.69 (t, 1H, J=6.0 Hz), 4.39 (d, 2H, J=6.0 Hz), 2.28 (s, 3H).

Preparation of compound RX-1144—Reaction of compound 4b with 4-bisphenyl-carboxaldehyde as above, preparation of compound 5b, followed by chromatography on SiO$_2$, gave compound RX-1144. $^1$H-NMR (300 MHz, d$_6$-DMSO): δ 9.40 (s, 1H), 8.38 (s, 1H), 8.17 (s, 1H), 7.89 (d, 1H, J=6.0 Hz), 7.66 (m, 4H), 7.56 (m, 3H), 7.36 (m, 6H), 7.24 (s, 1H), 6.81 (t, 1H, J=6.0 Hz), 4.50 (d, 2H, J=9.0 Hz).

Preparation of compound RX-1145—Reaction of compound 4b with 1,4-benzodioxane-6-carboxaldehyde as above, preparation of compound 5b, followed by chromatography on SiO$_2$, gave compound RX-1145. $^1$H-NMR (300 MHz, CDCl$_3$): δ 8.59 (s, 1H), 7.96 (s, 1H), 7.83 (s, 1H), 7.65 (m, 2H), 7.15 (m, 3H), 6.80 (m, 4H), 4.46 (s, 1H), 4.22 (s, 4H), 4.11 (s, 2H).

Preparation of compound RX-1146—Reaction of compound 4b with 3-(4-chlorophenoxy)benzaldehyde as above, preparation of compound 5b, followed by chromatography on SiO$_2$, gave compound RX-1146. $^1$H-NMR (300 MHz, d$_6$-DMSO): δ 9.35 (s, 1H), 8.39 (s, 1H), 8.14 (s, 1H), 7.86 (d, 1H, J=6.0 Hz), 7.56 (d, 1H, J=6.0 Hz), 7.32 (m, 8H), 7.13 (s, 1H), 6.94 (m, 3H), 6.83 (t, 1H, J=7.0 Hz), 4.46 (d, 2H, J=6.0 Hz).

Preparation of compound RX-1147—Reaction of compound 4a with 2-nitrobenzaldehyde as above, preparation of compound 5b, followed by chromatography on SiO$_2$, gave compound RX-1147. $^1$H-NMR (300 MHz, d$_6$-DMSO): δ 9.35 (s, 1H), 8.35 (s, 1H), 8.09 (m, 2H), 7.67 (m, 3H), 7.56 (m, 2H), 7.37 (m, 2H), 7.14 (s, 1H), 6.89 (t, 1H, J=6.0 Hz), 4.80 (d, 2H, J=6.0 Hz).

Example 2

4-Substituted amino quinazoline Compounds

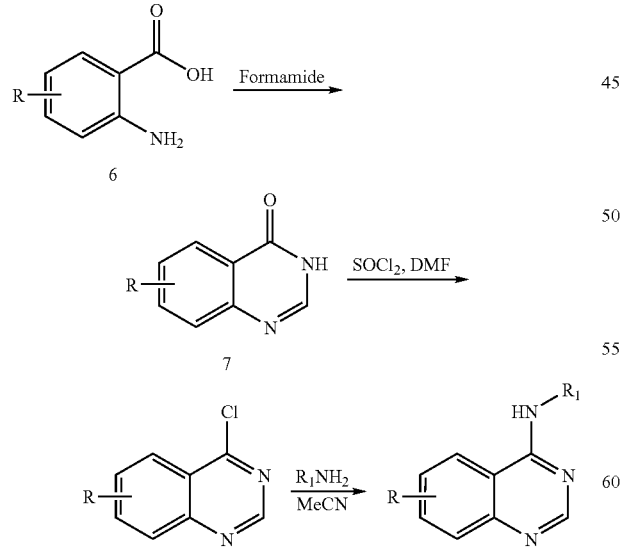

Scheme 2

R: a = 6-NO$_2$, b = 6-H, c = 6-Br, d = 7-F, e = 5-Me, f = 6-I

TABLE 3

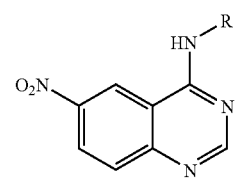

| Compd. No. RX- | R |
|---|---|
| 1122 | 2,4,6-trimethylphenyl (H$_3$C, CH$_3$, H$_3$C substituted phenyl) |
| 1123 | —CH(CH$_3$)—phenyl |
| 1137 | —(CH$_2$)$_2$—(3-fluorophenyl) |

TABLE 4

| Compd. No. RX- | R |
|---|---|
| 0183 | —(CH$_2$)$_4$—phenyl |
| 1160 | —CH(CH$_3$)—phenyl |
| 1169 | —(CH$_2$)$_2$—phenyl |
| 1195 | —(CH$_2$)$_2$—(3-fluorophenyl) |

TABLE 5

6-bromoquinazoline-4-amine core with HN-R substituent

| Compd. No. RX- | R |
|---|---|
| 1230 | naphthalen-1-ylmethyl (—CH₂-naphthyl) |
| 1236 | —CH(CH₃)-phenyl |
| 1242 | —(CH₂)₂-(3-fluorophenyl) |
| 1243 | —(CH₂)₂-phenyl |
| 1251 | —(CH₂)₄-phenyl |
| 1260 | —CH₂-(2-trifluoromethylphenyl) |
| 1277 | —(4-fluorophenyl) |
| 1279 | —(2-fluoro-4-chlorophenyl) |

TABLE 6

7-fluoroquinazoline-4-amine core with HN-R substituent

| Compd. No. RX- | R |
|---|---|
| 1294 | —(CH₂)₂-(4-fluorophenyl) |
| 1297 | —(CH₂)₂-phenyl |

TABLE 7

5-methylquinazoline-4-amine core with HN-R substituent

| Compd. No. RX- | R |
|---|---|
| 1541 | —(CH₂)₂-(4-fluorophenyl) |
| 1567 | —CH(CH₃)-phenyl |
| 1573 | —(CH₂)₄-phenyl |

TABLE 8

6-iodoquinazoline-4-amine core with HN-R substituent

| Compd. No. RX- | R |
|---|---|
| 1656 | —CH₂-(3-trifluoromethylphenyl) |
| 1659 | cyclohexyl |

TABLE 8-continued

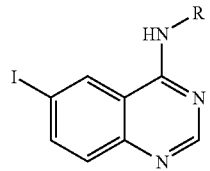

| Compd. No. RX- | R |
|---|---|
| 1664 | 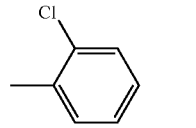 |
| 1668 |  |
| 1670 | 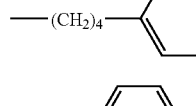 |
| 1674 | 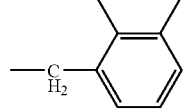 |
| 1675 | 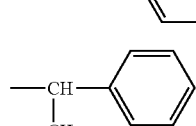 |
| 1679 | 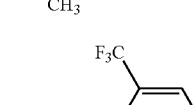 |
| 1682 | 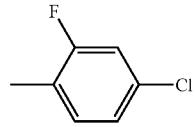 |
| 1701 | 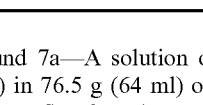 |

Preparation of compound 7a—A solution of 18.2 g of compound 6a (100 mmol) in 76.5 g (64 ml) of formamide (1.7 mol) was heated under reflux for 4 hrs at 120~125° C. Solvent was removed under reduced pressure and the crude solid was recrystallized from ethyl alcohol to give 12.7 g of compound 7a (yield, 87%). $^1$H-NMR (300 MHz, $d_6$-DMSO): δ 8.13 (m, 2H), 7.84 (m, 1H), 7.68 (m, 1H), 7.55 (m, 1H).

Preparation of compound 8a—To 7.3 g of compound 7a (50 mmol) was added dropwise 230 ml of thionyl chloride (2 mol) at 0° C. with stirring. To a mixture was added 2~3 drops of N,N-dimethylformamide and heated under reflux for 3~4 hrs. Thionyl chloride was removed under reduced pressure and the resulting residue was washed with sodium carbonate. The product was extracted with ethyl acetate and the organic layer was dried over MgSO$_4$ and concentrated under reduced pressure. The crude product was purified by SiO$_2$ column chromatography (silica gel; 230-400 mesh) to give 6.47 g of compound 8a (yield, 79%). $^1$H-NMR (300 MHz, $d_6$-DMSO): δ 9.03 (s, 1H), 8.18 (m, 1H), 7.99 (m, 1H), 7.89 (m, 1H), 7.70 (m, 1H).

Preparation of compound RX-1122—A solution of 30 mg of compound 8a (0.18 mmol) and 1.2 eq of 2,4,6-trimethyl aniline in acetonitrile was heated under reflux for 8 hrs. The organic solvent was removed under reduced pressure and the crude solid was purified by SiO$_2$ column chromatography (silica gel; 230-400 mesh) to give compound RX-1122. $^1$H-NMR (300 MHz, CDCl$_3$): δ 9.08 (s, 1H), 8.74 (s, 1H), 8.56 (d, 1H, J=9.0 Hz), 8.00 (d, 1H, J=3.0 Hz), 7.71 (s, 1H), 7.03 (s, 2H), 2.35 (s, 3H), 2.23 (s, 6H).

Preparation of compound RX-1123—Reaction of compound 8a with α-methylbenzylamine as above, preparation of compound RX-1122, followed by chromatography on SiO$_2$, gave compound RX-1123. $^1$H-NMR (300 MHz, CDCl$_3$): δ 8.76 (s, 1H), 8.52 (d, 1H, J=6.0 Hz), 7.94 (d, 1H, J=9.0 Hz), 7.42 (m, 5H), 6.26 (d, 1H, J=9.0 Hz), 5.69 (t, 1H, J=9.0 Hz), 1.76 (d, 3H, J=6.0 Hz).

Preparation of compound RX-1137—Reaction of compound 8a with 3-fluorophenethylamine as above, preparation of compound RX-1122, followed by chromatography on SiO$_2$, gave compound RX-1137. $^1$H-NMR (300 MHz, CDCl$_3$): δ 8.80 (s, 1H), 8.63 (s, 1H), 8.53 (d, 1H, J=9.0 Hz), 7.96 (d, 1H, J=9.0 Hz), 7.33 (m, 1H), 7.02 (m, 3H), 6.11 (s, 1H), 4.02 (q, 2H, J=15.0 Hz, J=6.0 Hz).

Preparation of compound RX-1160—Reaction of compound 8b with α-methylbenzylamine as above, preparation of compound RX-1122, followed by chromatography on SiO$_2$, gave compound RX-1160. $^1$H-NMR (300 MHz, CDCl$_3$): δ 8.68 (s, 1H), 7.86 (d, 1H, J=8.24 Hz), 7.75 (m, 2H), 7.50-7.31 (m, 6H), 5.92 (d, 1H, J=6.08 Hz), 5.66 (t, 1H, J=6.90 Hz), 1.72 (m, 3H).

Preparation of compound RX-1169—Reaction of compound 8b with phenethylamine as above, preparation of compound RX-1122, followed by chromatography on SiO$_2$, gave compound RX-1169. $^1$H-NMR (300 MHz, CDCl$_3$): δ 8.71 (s, 1H), 7.87 (d, 1H, J=6.0 Hz), 7.75 (t, 1H, J=3.0 Hz), 7.54 (d, 1H, J=6.0 Hz), 7.35 (m, 5H), 5.78 (s, 1H), 3.97 (t, 2H, J=9.0 Hz), 3.06 (t, 2H, J=9.0 Hz).

Preparation of compound RX-0183—Reaction of compound 8b with 4-phenylbutylamine as above, preparation of compound RX-1122, followed by chromatography on SiO$_2$, gave compound RX-0183. $^1$H-NMR (300 MHz, CDCl$_3$): δ 8.68 (s, 1H), 7.82 (d, 1H, J=9.0 Hz), 7.70 (t, 1H, J=7.0 Hz), 7.39 (t, 1H, J=6.0 Hz), 7.27 (d, 1H, J=6.0 Hz), 7.21 (m, 5H), 6.21 (s, 1H) 3.72 (d, 2H, J=3.0 Hz), 2.77 (t, 2H, J=9.0 Hz), 2.08 (t, 2H, J=8.0 Hz).

Preparation of compound RX-1195—Reaction of compound 8b with 3-fluorophenethylamine as above, preparation of compound RX-1122, followed by chromatography on SiO$_2$, gave compound RX-1195. $^1$H-NMR (300 MHz, CDCl$_3$): δ 8.70 (s, 1H), 7.84 (d, 1H, J=9.0 Hz), 7.74 (t, 1H, J=7.0 Hz), 7.61 (d, 1H, J=6.0 Hz), 7.44 (t, 1H, J=3.0 Hz), 7.28 (t, 1H, J=9.0 Hz), 7.02 (m, 3H), 5.95 (s, 1H), 3.96 (t, 2H, J=9.0 Hz), 3.05 (t, 2H, J=9.0 Hz).

Preparation of compound RX-1230—Reaction of compound 8c with 1-naphthalenemethylamine as above, preparation of compound RX-1122, followed by chromatography on SiO$_2$, gave compound RX-1230. $^1$H-NMR (300 MHz, CDCl$_3$): δ 8.79 (s, 1H), 8.06 (t, 1H, J=9.0 Hz), 7.93 (m, 2H), 7.77 (m, 3H), 7.54 (m, 4H), 5.88 (s, 1H), 5.28 (s, 2H).

Preparation of compound RX-1236—Reaction of compound 8c with α-methylbenzylamine as above, preparation of compound RX-1122, followed by chromatography on SiO$_2$, gave compound RX-1236. $^1$H-NMR (300 MHz, CDCl$_3$): δ 8.65 (s, 1H), 7.92 (s, 1H), 7.77 (d, 1H, J=9.0 Hz), 7.70 (d, 1H, J=9.0 Hz), 7.37 (m, 5H), 6.09 (d, 1H, J=9.0 Hz), 5.64 (t, 1H, J=6.0 Hz), 1.70 (s, 3H).

Preparation of compound RX-1242—Reaction of compound 8c with 3-fluorophenethylamine as above, preparation of compound RX-1122, followed by chromatography on SiO$_2$, gave compound RX-1242. $^1$H-NMR (300 MHz, CDCl$_3$): δ 8.69 (s, 1H), 7.79 (m, 2H), 7.70 (d, 1H, J=9.0 Hz), 7.28 (t, 1H, J=8.0 Hz), 6.96 (m, 3H), 5.94 (s, 1H), 3.92 (m, 2H), 3.05 (t, 2H, J=6.0 Hz).

Preparation of compound RX-1243—Reaction of compound 8c with phenethylamine as above, preparation of compound RX-1122, followed by chromatography on SiO$_2$, gave compound RX-1243. $^1$H-NMR (300 MHz, CDCl$_3$): δ 8.69 (s, 1H), 7.75 (m, 3H), 7.36 (m, 2H), 7.28 (m, 3H), 5.86 (s, 1H), 3.93 (t, 2H, J=6.0 Hz), 3.05 (t, 2H, J=6.0 Hz).

Preparation of compound RX-1251—Reaction of compound 8c with 4-phenylbutylamine as above, preparation of compound RX-1122, followed by chromatography on SiO$_2$, gave compound RX-1251. $^1$H-NMR (300 MHz, CDCl$_3$): δ 8.67 (s, 1H), 7.87 (d, 1H, J=15.5 Hz), 7.79 (m. 2H), 7.30 (m, 2H), 7.20 (m, 3H), 5.93 (s, 1H), 3.68 (t, 2H, J=9.0 Hz), 2.69 (t, 2H, J=9.0 Hz), 1.77 (m, 4H).

Preparation of compound RX-1260—Reaction of compound 8c with 2-(trifluoromethyl)benzylamine as above, preparation of compound RX-1122, followed by chromatography on SiO$_2$, gave compound RX-1260. $^1$H-NMR (300 MHz, CDCl$_3$): δ 8.66 (s, 1H), 7.96 (s, 1H), 7.79 (t, 1H, J=6.0 Hz), 7.63 (m. 3H), 7.52 (t, 1H, J=6.0 Hz), 7.39 (t, 1H, J =6.0 Hz), 6.51 (s, 1H), 5.07 (d, 1H, J=3.0 Hz).

Preparation of compound RX-1277—Reaction of compound 8c with 4-fluoroaniline as above, preparation of compound RX-1122, followed by chromatography on SiO$_2$, gave compound RX-1277. $^1$H-NMR (300 MHz, CDCl$_3$): δ 8.75 (s, 1H), 8.10 (s, 1H), 7.88 (d, 1H, J=9.0 Hz), 7.80 (d, 1H, J=9.0 Hz), 7.68 (m, 2H), 7.56 (s, 1H), 7.13 (t, 1H, J=6.0 Hz).

Preparation of compound RX-1279—Reaction of compound 8c with 4-chloro-2-fluoroaniline as above, preparation of compound RX-1122, followed by chromatography on SiO$_2$, gave compound RX-1279. $^1$H-NMR (300 MHz, CDCl$_3$): δ 8.80 (s, 1H), 8.48 (t, 1H, J=6.0 Hz), 8.07 (s, 1H) 7.89 (d, 1H, J=6.0 Hz), 7.80 (d, 1H, J=9.0 Hz), 7.68 (S, 1H), 7.22(m, 2H).

Preparation of compound RX-1294—Reaction of compound 8d with 4-fluorophenethylamine as above, preparation of compound RX-1122, followed by chromatography on SiO$_2$, gave compound RX-1294. $^1$H-NMR (300 MHz, CDCl$_3$): δ 8.65 (s, 1H), 7.65 (t, 1H, J=3.0 Hz), 7.45 (t, 1H, J=6.0 Hz), 7.28 (d, 1H, J=6.0 Hz), 7.20 (t, 1H, J=5.0 Hz), 6.97 (m, 3H), 6.07 (s, 1H), 3.94 (m, 2H), 3.04 (t, 2H, J=9.0 Hz).

Preparation of compound RX-1297—Reaction of compound 8d with phenethylamine as above, preparation of compound RX-1122, followed by chromatography on SiO$_2$, gave compound RX-1297. $^1$H-NMR (300 MHz, CDCl$_3$): δ 8.65 (s, IH), 7.60 (t, 1H, J=6.0 Hz), 7.42 (t, 1H, J=6.0 Hz), 7.32 (m, 2H), 7.28 (m, 3H), 7.16 (t, 1H, J=6.0 Hz), 6.02 (s, 1H), 3.92 (m, 2H), 3.04 (t, 2H, J=9.0 Hz).

Preparation of compound RX-1541—Reaction of compound 8e with 4-fluorophenethylamine as above, preparation of compound RX-1122, followed by chromatography on SiO$_2$, gave compound RX-1541. $^1$H-NMR (300 MHz, CDCl$_3$): δ 8.06 (s, 1H), 7.66 (t, 1H, J=6.0 Hz), 7.52 (t, 1H, J=6.0 Hz), 7.30 (t, 1H, J=6.0 Hz), 7.15 (d, 1H, J=9.0 Hz), 7.01 (m. 3H), 6.02 (s, 1H), 3.96 (m, 2H), 3.06 (t, 2H, J=9.0 Hz), 2.61 (s, 3H).

Preparation of compound RX-1567—Reaction of compound 8e with α-methylbenzylamine as above, preparation of compound RX-1122, followed by chromatography on SiO$_2$, gave compound RX-1567. $^1$H-NMR (300 MHz, CDCl$_3$): δ 8.56 (s, 1H), 7.68 (d, 1H, J=6.0 Hz), 7.55 (t, 1H, J=6.0 Hz), 7.36 (m, 4H), 7.21 (t, 1H, J=6.0 Hz), 7.19 (t, 1H, J=7.0 Hz), 6.31 (s, 1H), 5.60 (t, 1H, J=7.0 Hz), 2.90 (s, 3H), 1.68 (d, 3H, J=9.0 Hz).

Preparation of compound RX-1573—Reaction of compound 8e with 4-phenylbutylamine as above, preparation of compound RX-1122, followed by chromatography on SiO$_2$, gave compound RX-1573. $^1$H-NMR (300 MHz, CDCl$_3$): δ 8.58 (s, 1H), 7.71 (d, 1H, J=9.0 Hz), 7.55 (t, 1H, J=6.0 Hz), 7.30 (t, 1H, J=6.0 Hz), 7.18 (m, 5H), 6.10 (s, 1H), 3.66 (d, 2H, J=6.0 Hz), 2.84 (s, 3H), 2.70 (d, 2H, J=6.0 Hz), 1.78 (m 4H).

Preparation of compound RX-1656—Reaction of compound 8f with 3-(trifluoromethyl)benzylamine as above, preparation of compound RX-1122, followed by chromatography on SiO$_2$, gave compound RX-1656. $^1$H-NMR (300 MHz, d$_6$-Aectone): δ 8.61 (d, 1H, J=6.0 Hz), 8.55 (s, 1H), 8.30 (s, 1H), 8.05 (t, 1H, J=8.0 Hz), 7.77 (m, 2H), 7.56 (m, 3H), 5.00 (d, 2H, J=3.0 Hz).

Preparation of compound RX-1659—Reaction of compound 8f with cyclohexylamine as above, preparation of compound RX-1122, followed by chromatography on SiO$_2$, gave compound RX-1659. $^1$H-NMR (300 MHz, d$_6$-Aectone): δ 8.55 (d, 1H, J=3.0 Hz), 8.51 (s, 1H), 8.00 (m, 1H), 7.50 (d, 1H, J=9.0 Hz), 7.38 (d, 1H, 0.02), 4.28 (t, 1H, J=8.0 Hz), 2.07 (m, 4H), 1.80 (m, 3H), 1.39 (m, 3H).

Preparation of compound RX-1664—Reaction of compound 8f with 2-chloroaniline as above, preparation of compound RX-1122, followed by chromatography on SiO$_2$, gave compound RX-1664. $^1$H-NMR (300 MHz d$_6$-Aectone): δ 7.41 (d, 1H, J=6.0 Hz), 7.20 (s, 1H), 6.82 (t, 1H, J=6.0 Hz), 6.24 (d, 1H, J=6.0 Hz), 6.13 (m, 2H), 6.00 (m, 2H).

Preparation of compound RX-1668—Reaction of compound 8f with 3-fluorophenethylamine as above, preparation of compound RX-1122, followed by chromatography on SiO$_2$, gave compound RX-1668. $^1$H-NMR (300 MHz d$_6$-Aectone): δ 8.53 (d, 1H, J=12.0 Hz), 8.48 (s, 1H), 8.00 (t, 1H, J=7.0 Hz), 7.85 (s, 1H), 7.50 (d, 1H, J=9.0 Hz), 7.30 (m, 1H), 7.09 (m, 2H), 6.93 (m, 1H), 3.90 (m, 2H), 3.00 (m, 2H).

Preparation of compound RX-1670—Reaction of compound 8f with 4-phenylbutylamine as above, preparation of compound RX-1122, followed by chromatography on SiO$_2$, gave compound RX-1670. $^1$H-NMR (300 MHz, d$_6$-Aectone): δ 8.51 (s, 2H), 8.01 (t, 1H, J=6.0 Hz), 7.67 (s, 1H), 7.50 (d, 1H, J=9.0 Hz), 7.20 (m, 5H), 3.68 (m, 2H), 2.66 (t, 2H, J=6.0 Hz), 1.74 (m, 4H).

Preparation of compound RX-1674—Reaction of compound 8f with 1-naphthalenemethylamine as above, preparation of compound RX-1122, followed by chromatography on SiO$_2$, gave compound RX-1674. $^1$H-NMR (300 MHz, CDCl$_3$): δ 8.77 (s, 1H), 8.00 (d, 1H, J=6.0 Hz), 7.94 (m, 4H), 7.53 (m, 5H), 5.84 (s, 1H), 5.37 (d, 2H, J=3.0 Hz).

Preparation of compound RX-1675—Reaction of compound 8f with phenethylamine as above, preparation of compound RX-1122, followed by chromatography on SiO$_2$, gave compound RX-1675. $^1$H-NMR (300 MHz, CDCl$_3$): δ 8.61 (s, 1H), 7.94 (m, 2H), 7.55 (t, 1H, J=6.0 Hz), 7.32 (m, 5H), 5.93 (s, 1H), 3.90 (m, 2H), 3.03 (t, 2H, J=9.0 Hz).

Preparation of compound RX-1679—Reaction of compound 8f with α-methylbenzylamine as above, preparation of compound RX-1122, followed by chromatography on SiO$_2$, gave compound RX-1679. $^1$H-NMR (300 MHz, CDCl$_3$): δ 8.65 (d, 1H, J=3.0 Hz), 8.08 (s, 1H), 7.92 (d, 1H, J=9.0 Hz), 7.53 (m, 1H), 7.38 (m, 5H), 6.00 (d, 1H, J=6.0 Hz), 5.61 (t, 1H, J=9.0 Hz), 1.67 (m, 3H).

Preparation of compound RX-1682—Reaction of compound 8f with 2-(trifluoromethyl)benzylamine as above, preparation of compound RX-1122, followed by chromatography on SiO$_2$, gave compound RX-1682. $^1$H-NMR (300 MHz, CDCl$_3$): δ 8.70 (s, 1H), 8.07 (s, 1H), 7.97 (t, 1H, J=6.0 Hz), 7.58 (m, 5H), 6.16 (s, 1H), 5.08 (t, 2H, J=9.0 Hz).

Preparation of compound RX-1701—Reaction of compound 8f with 4-chloro-2-fluoroaniline as above, preparation of compound RX-1122, followed by chromatography on SiO$_2$, gave compound RX-1701. $^1$H-NMR (300 MHz, d$_6$-DMSO): δ 9.35 (s, 1H), 8.95 (s, 1H), 8.40 (d, 1H, J=9.0 Hz), 7.80 (d, 1H, J=9.0 Hz), 7.69 (d, 1H, J=12.0 Hz), 7.59 (t, 1H, J=9.0 Hz), 7.45 (d, 1H, J=9.0 Hz).

Example 3

6,7-Dimethoxy-4-Substituted amino quinazoline Compounds

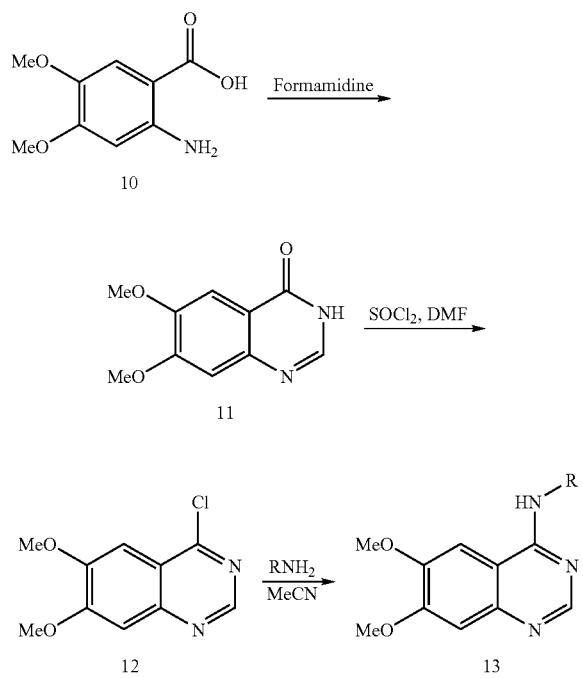

Scheme 3

TABLE 9

| Compd. No. RX- | R |
|---|---|
| 1707 | —CH(CH$_3$)—phenyl |
| 1715 | —(CH$_2$)$_4$—phenyl |
| 1728 | —(CH$_2$)$_2$—(3-fluorophenyl) |

Preparation of compound 11—A solution of 9.85 g of compound 10 (5 mmol) and 6.8 g of formamidine hydrochloride (85 mmol) was heated under reflux for 15 min at 210° C. After cooling to 80° C., the solution was basified with saturated sodium hydroxide and washed with n-hexane and water to give 6.59 g of compound 11 (yield, 64%). $^1$H-NMR (300 MHz, d$_6$-DMSO): δ 7.98 (s, 1H), 7.42 (s, 1H), 7.11 (s, 1H), 3.89 (d, 6H).

Preparation of compound 12—Compound 11, 2.06 g, (10 mmol) was added dropwise to 47 ml of thionyl chloride (0.4 mol) at 0° C. with stirring. To a mixture was added 2~3 drops of N,N-diniethylformamide and heated under reflux for 3~4 hrs. Thionyl chloride was remioved under reduced pressure and the resulting residue was washed with sodium carbonate. The product was extracted with ethyl acetate and the organic layer was dried over MgSO$_4$ and concentrated under reduced pressure. The crude product was purified by SiO$_2$ column chromatography (silica gel; 230-400 mesh) to give 0.58 g of compound 12 (yield, 26%). $^1$H-NMR (300 MHz, d$_6$-DMSO): δ 8.88 (s, 1H), 7.46 (s, 1H), 7.40 (s, 1H), 4.01 (d, 6H).

Preparation of compound RX-1707—A solution of 30 mg of compound 12 (0.13 mmol) and 1.2 eq of α-methyl benzylamine in acetonitrile was heated under reflux for 8 hrs. The organic solvent was removed under reduced pressure and the crude solid was purified by SiO$_2$ column chromatography (silica gel; 230-400 mesh) to give compound RX-1707. $^1$H-NMR (300 MHz, CDCl$_3$): δ 8.56 (s, 1H), 7.47 (d, 2H, J=6.0 Hz), 7.36 (m, 3H), 7.20 (s, 1H), 6.86 (s, 1H), 5.65 (s, 1H), 5.55 (s, 1H), 3.99 (s, 6H), 1.70 (m, 3H).

Preparation of compound RX-1715—Reaction of compound 12 with 4-phenylbutylamine as above, preparation of compound RX-1707, followed by chromatography on SiO$_2$, gave compound RX-1715. $^1$H-NMR (300 MHz, CDCl$_3$): δ 8.56 (s, 1H), 7.27 (t, 2H, J=9.0 Hz), 7.20 (m, 4H), 6.94 (s, 1H), 5.82 (s, 1H), 3.93 (s, 6H), 3.67 (d, 2H, J=6.0 Hz), 2.67 (m, 2H), 1.75 (m, 4H).

Preparation of compound RX-1728—Reaction of compound 12 with 3-fluorophenethylamine as above, preparation of compound RX-1707, followed by chromatography on SiO$_2$, gave compound RX-1728. $^1$H-NMR (300 MHz, CDCl₃): δ 8.57 (s, 1H), 7.28 (t, 1H, J=6.0 Hz), 7.17 (s, 1H), 6.99 (d, 1H, J=9.0 Hz), 6.92 (m, 3H), 6.04 (s, 1H), 3.90 (m, 8H), 3.03 (t, 2H, J=12.0 Hz).

Example 4

6,7-Diethoxy-4-Substituted amino guinazoline Compounds

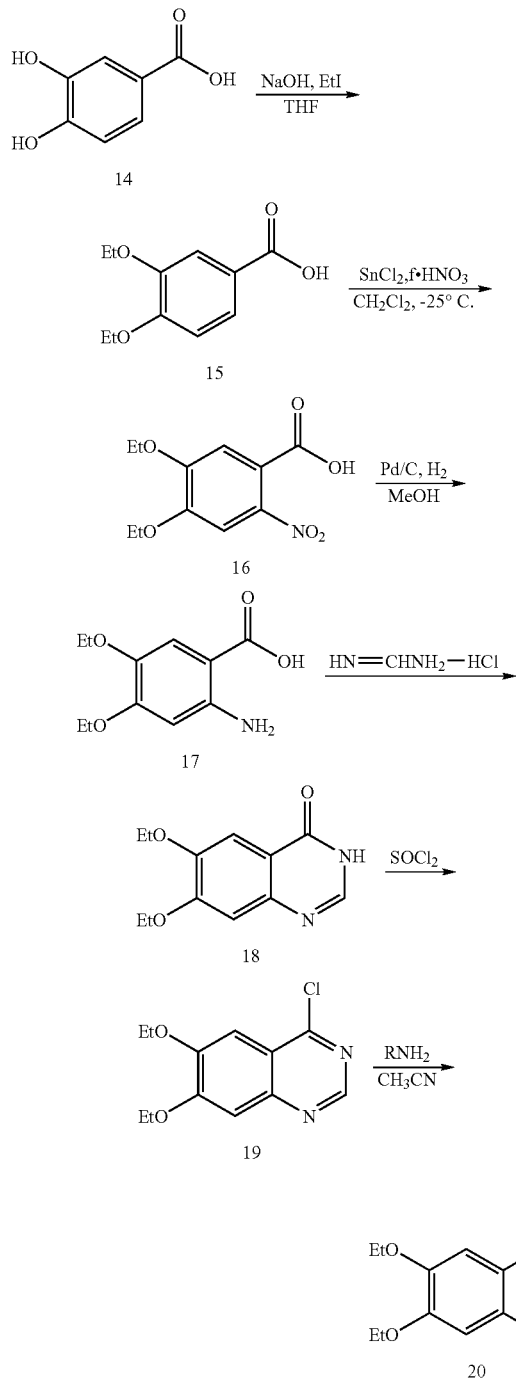

Scheme 4

TABLE 10

| Compd. No. RX- | R |
|---|---|
| 1758 | —CH(CH₃)—C₆H₅ |
| 1763 | —CH₂—(3-CF₃-C₆H₄) |
| 1766 | —(CH₂)₂—C₆H₅ |
| 1767 | —(CH₂)₄—C₆H₅ |
| 1777 | —CH₂—(3,5-(OCH₃)₂-C₆H₃) |
| 1779 | —CH₂—(2-F-C₆H₄) |
| 1792 | —CH₂—(2-F-6-Cl-C₆H₃) |
| 1798 | —CH₂—(2-Cl-C₆H₄) |
| 1799 | —CH₂—(4-Cl-C₆H₄) |

Preparation of compound 15—To 30 g of 3,4-Dihydroxybenzoic acid (0.19 mol) in 90 ml of anhydrous tetrahydrofuran was added 225 ml of 4.0 M sodium hydroxide at 0° C. with stirring, followed by adding dropwise 32.7 ml of ethyl iodide (0.409 mol) at 0° C. with stirring. The mixture was stirred for 5 min at room temperature and was heated at 100° C. until TLC did not detect the starting material. After cooling and washing with n-hexane, the solution was acidified to pH 2 with 1N-HCl and washed with ethyl acetate to give 37 g of compound 15 (yield, 90%). $^1$H-NMR (300 MHz, CDCl$_3$): δ 7.28 (s, 1H), 6.82 (s, 1H), 6.71 (s, 1H), 4.13 (m, 4H), 1.46 (m, 6H).

Preparation of compound 16—To a mixture of 11.4 ml of Tin(IV) chloride (0.097 mol) and 0.1 ml of fumming nitric acid (0.155 mol) in 100 ml of dichloromethane was added dropwise 17 g of compound 15 (0.08 mol) in 100 ml of dichloromethane at −25° C. with stirring. After 5 min, 200 ml of water was added and the product was extracted with dichloromethane and ethyl acetate. The organic layer was dried over MgSO$_4$ and concentrated to give compound 16 (16.4 g, 85%). $^1$H-NMR (300 MHz, CDCl$_3$): δ 7.28 (s, 1H), 6.82 (s, 1H), 4.13 (m, 4H), 1.46 (m, 6H).

Preparation of compound 17—A solution of compound 16 (8 g, 0.033 mol). in methyl alcohol (30 ml) was hydrogenated over 5% Pd/C and filtered through Celite. Solvent was evaporated under reduced pressure and the crude residue was purified by SiO$_2$ colunm chromatography (silica gel; 230-400 mesh) to give compound 17 (5.0 g, 67%). $^1$H-NMR (300 MHz, CDCl$_3$): δ 7.28 (s, 1H), 7.12 (s, 2H), 6.14 (s, 1H), 4.13 (m, 4H), 1.46 (m, 6H).

Preparation of compound 18—A solution of compound 17 (5 g, 0.22 mol) and formamidine hydrochloride (500 mg, 0.356 mol) was heated under reflux for 15 min at 210° C. , After cooling to 80° C., the solution was basified with 0.33 M sodium hydroxide (5 ml) and washed with n-hexane and water to give compound 18 (4.2 g, 81%). $^1$H-NMR (300 MHz, d$_6$-D)MSO): δ 8.27 (s, 1H), 7.42 (s, 1H) 7.09 (s, 1H), 4.19 (m, 4H), 1.38 (m, 6H).

Preparation of compound 19—To 4.2 g of compound 18 (18 mmol) was added dropwise 52 ml of thionyl chloride (0.72 mol) at 0° C. with stirring. Thionyl chloride was removed under reduced pressure and the resulting residue was washed with sodium carbonate. The product was extracted with ethyl acetate and the organic layer was dried over MgSO$_4$ and concentrated under reduced pressure. The crude product was purified by SiO$_2$ column chromatography (silica gel; 230-400 mesh) to give 1.5 g of compound 19 (yield, 33%). $^1$H-NMR (300 MHz, d$_6$-DMSO): δ 8.27 (s, 1H), 7.42 (s, 1H) 7.09 (s, 1H), 4.19 (m, 4H), 1.38 (m, 6H).

Preparation of compound RX-1758—A solution of compound 19 and 1.2 eq of α-methylbenzylamine in acetonitrile was heated under reflux for 8 hrs at 100° C. Solvent was evaporated under reduced pressure and the crude residue was purified by SiO$_2$ column chromatography (silica gel; 230-400 mesh) to give compound RX-1758. $^1$H-NMR (300 MHz, CDCl$_3$): δ 8.51 (s, 1H), 7.78 (s, 1H), 7.36 (m, 5), 6.89 (s, 1H), 5.66 (m, 1H), 4.18 (m, 4H), 1.53 (m, 6H), 0.85 (m, 3H).

Preparation of compound RX-1763—Reaction of compound 19 with 3-(trifluoromethyl)benzylamine as above, preparation of compound RX-1758, followed by chromatography on SiO$_2$, gave compound RX-1763. $^1$H-NMR (300 MHz, d$_6$-DMSO): δ 8.50 (s, 1H), 8.29 (s, 1H), 7.62 (m, 5H), 7.07 (s, 1H), 4.82 (d, 2H, J=3.0 Hz), 4.13 (m, 4H), 1.35 (m, 6H).

Preparation of compound RX-1766—Reaction of compound 19 with phenethylamine as above, preparation of compound RX-1758, followed by chromatography on SiO$_2$, gave compound RX-1766. $^1$H-NMR (300 MHz, CDCl$_3$): δ 8.71 (s, 1H), 7.43 (m, 5H), 7.32 (s, 1H), 6.89 (s, 1H), 4.37 (m, 2H), 4.22 (m, 2H), 4.07 (m, 2H), 3.18 (t, 2H, J=12.0 Hz), 1.65 (m, 6H).

Preparation of compound RX-1767—Reaction of compound 19 with 4-phenylbutylamine as above, preparation of compound RX-1758, followed by chromatography on SiO$_2$, gave compound RX-1767. $^1$H-NMR (300 MHz, CDCl$_3$): δ 8.70 (s, 1H), 7.42 (m, 6H), 7.00 (s, 1H), 5.55 (s, 1H), 4.36 (m, 4H), 3.82 (d, 2H, J=6.0 Hz), 2.86 (d, 2H, J=0.02 Hz), 1.87 (m, 4H), 1.68 (m, 6H).

Preparation of compound RX-1777—Reaction of compound 19 with 3,5-dimethoxybenzylamine as above, preparation of compound RX-1758, followed by chromatography on SiO$_2$, gave compound RX-1777. $^1$H-NMR (300 MHz, CDCl$_3$): δ 8.58 (s, 1H), 7.28 (s, 1H), 7.19 (s, 1H), 6.92 (s, 1H), 6.56 (d, 1H, J=3.0 Hz), 6.41 (s, 1H), 4.79 (d, 2H, J=6.0 Hz), 4.22 (m, 4H), 3.78 (s, 6H), 1.52 (m, 6H).

Preparation of compound RX-1779—Reaction of compound 19 with 2-fluorobenzylamirie as above, preparation of compound RX-1758, followed by chromatography on SiO$_2$, gave compound RX-1779. $^1$H-NMR (300 MHz, CDCl$_3$): δ 8.58 (s, 1H), 7.48 (t, 1H, J=8.0 Hz), 7.15 (m, 4H); 6.92, (s, 1H), 5.87 (s, 1H), 4.93 (d, 2H, J=6.0 Hz), 4.18 (m, 4H), 1.53 (m, 6H).

Preparation of compound RX-1792—Reaction of compound 19 with 2-chloro-6-fluorobenzylamine as above, preparation of compound RX-1758, followed by. chromatography on SiO$_2$, gave compound RX-1792. $^1$H-NMR (300 MHz, CDCl$_3$): δ 8.59 (s, 1H), 7.19 (m, 3H), 6.96 (m, 2H), 5.91 (s, 1H), 5.01 (m, 2H), 4.19 (t, 2H, J=8.0 Hz), 4.05 (t, 2H, J=9.0 Hz), 1.50 (m, 6H).

Preparation of compound RX-1798—Reaction of compound 19 with 2-chlorobenzylamiine as above, preparation of compound RX-1758, followed by chromatography on Sio$_2$, gave compound RX-1798. $^1$H-NMR (300 MHz, d$_6$-DMSO): δ 8.28 (s, 1H), 7.69 (s, 1H), 7.45 (s, 1H), 7.28 (d, 2H, J=3.0 Hz), 7.09 (s, 1H), 4.81 (d, 2H, J=3.0 Hz), 4.16 (m, 4H), 1.37 (m, 6H).

Preparation of compound RX-1799—Reaction of compound 19 with 4-chlorobenzylamine as above, preparation of compound RX-1758, followed by chromatography on SiO$_2$, gave compound RX-1799. $^1$H-NMR (300 MHz, CDCl$_3$): δ 8.55 (s, 1H), 7.30 (m, 4H), 7.18 (s, 1H), 6.96 (s, 1H), 6.05 (s, 1H), 4.84 (d, 2H, J=3.0 Hz), 4.15 (m, 4H), 1.53 (m, 6H).

Example 5

3H-Imidazo[4.5-g]guinazoline Compounds

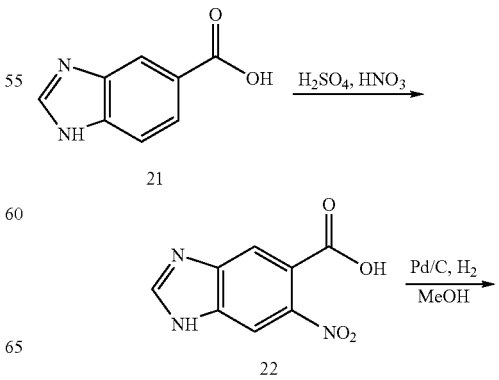

Scheme 5

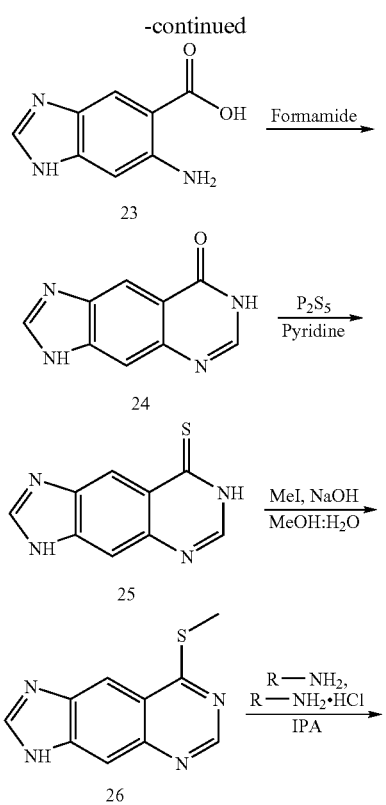

TABLE 11

| Compd. No RX- | R |
|---|---|
| 1805 | —⟨C₆H₄⟩—(CH₂)₃CH₃ |
| 1806 | —⟨C₆H₄⟩—CH(CH₃)₂ |
| 1807 | —⟨C₆H₄⟩—OCH₃ |
| 1810 | —⟨C₆H₄⟩—CH₂CH₃ |

TABLE 11-continued

| Compd. No RX- | R |
|---|---|
| 1813 | —(CH₂)₂—⟨3-F-C₆H₄⟩ |
| 1815 | —⟨C₆H₅⟩ |
| 1818 | —⟨2,4,6-(CH₃)₃-C₆H₂⟩ |
| 1819 | —⟨2-CH₃-C₆H₄⟩ |
| 1828 | —(CH₂)₂—⟨C₆H₅⟩ |
| 1834 | —CH(CH₃)₂ |
| 1835 | —(CH₂)₂—⟨C₆H₄⟩—CH₃ |
| 1840 | —CH(CH₃)—⟨C₆H₅⟩ |
| 1842 | —(CH₂)₄—⟨C₆H₅⟩ |

Preparation of compound 22—Compound 21 (10 g, 62 mmol) was added to a cooled solution of concentrated sulfuric acid (50 ml) and fuming nitric acid (50 ml) at 0° C. with stirring, and the mixture was stirred at room temperature, followed by heating under reflux for 1 hr, before being cooled and poured onto ice-water. The precipitate was collected to give compound 22 (8.47 g, 66%).

Preparation of compound 23—A solution of compound 22 (5 g, 0.024 mol) in dried methyl alcohol (80 ml) was hydrogenated over 5% Pd/C, filtered through Celite and washed with N,N-dimethylformamide. Solvent was evaporated under reduced pressure to give compound 23 (3.4 g, 82%).

Preparation of compound 24—A solution of compound 23 (4 g, 22.5 mmol) and formamide (1.8 mg, 38.3 mmol)

was heated under reflux for 2 hrs at 120~125° C. After cooling the product was recrystallized from ethyl alcohol to give compound 24 (3.6 g, 87%). $^1$H-NMR (300 MHz, d$_6$-DMSO): δ 8.78 (s, 1H), 8.52 (s, 1H), 8.34 (s, 1H), 7.98 (s, 1H).

Preparation of compound 25—A mixture of compound 24 (1.7 g, 9.1 mmol) and phosphorouspentasulfide (4.04 g, 18.2 mmol) in pyridine (80 ml) was heated under reflux for 16 hrs and the pyridine was removed under reduced pressure. The residue was treated with boiling water, and the yellow precipitate was collected by filtration and dissolved in 0.1 M NaOH solution. After filtration to remove insolubles, the solution was neutralized with NH$_4$Cl and the solvent was evaporated under reduced pressure to give compound 25 (1.0 g, 59%). $^1$H-NMR (300 MHz, d$_6$-DMSO): δ 8.87 (s, 1H), 8.61 (s, 1H), 8.09 (s, 1H), 7.81 (m, 1H).

Preparation of compound 26—To a solution of compound 25 (1 g, 4.93 mmol) and 1 N NaOH (6.9 ml) in 50% MeOH/water (50 ml) was added dropwise MeI (0.73 g, 5.1 mnmol) at 0° C., and the mixture was stirred at room temperature for 0.5~1 hr. The solution was neutralized with 1N hydrochloric acid and the solvent was removed under reduced pressure. The crude residue was purified by SiO$_2$ column chromatography (silica gel; 230-400 mesh) to give compound 26 (0.32 g, 39%). $^1$H-NMR (300 MHz, d$_6$-DMSO): δ 8.86 (s, 1H), 8.61 (s, 1H), 8.41 (s, 1H), 8.10 (s, 1H), 2.77 (s, 3H).

Preparation of compound RX-1805—A mixture of compound 26 (30 mg, 0.14 mmol), 1.5 eq of 4-butylaniline, and 1.5 eq of 4-butylaniline HCl in isopropyl alcohol (20 ml) was heated under reflux for 8 hrs. After cooling the solvent was removed under reduced pressure. The resulting residue was purified by SiO$_2$ column chromatography (silica gel; 230-400 mesh) to give compound RX-1805. $^1$H-NMR (300 MHz, CD$_{3OD}$): δ 8.75 (s, 1H), 8.55 (s, 1H), 8.44 (s, 1H), 7.95 (s, 1H), 7.60 (d, 2H, J=9.0 Hz), 7.00 (d, 2H, J=9.0 Hz), 2.65 (m, 2H), 2.05 (m, 2H), 1.33 (m, 2H), 0.96 (m, 3H).

Preparation of compound RX-1806—Reaction of compound 26 with p-isopropylaniline as above, preparation of compound RX-1805, followed by chromatography on SiO$_2$, gave compound RX-1806. $^1$H-NMR (300 MHz, CD$_3$OD): δ 8.75 (s, 1H), 8.55 (s, 1H), 8.44 (s, 1H), 7.95 (s, 1H), 7.60 (d, 2H, J=9.0 Hz), 7.00 (d, 2H, 0.03), 2.92 (m, 1H), 1.21 (s, 6H).

Preparation of compound RX-1807—Reaction of compound 26 with p-anisidine as above, preparation of compound RX-1805, followed by chromatography on SiO$_2$, gave compound RX-1807. $^1$H-NMR (300 MHz, CD$_3$OD): δ 8.75 (s, 1H), 8.55 (s, 1H), 8.44 (s, 1H), 7.95 (s, 1H), 7.60 (d, 2H, J=9.0 Hz), 7.00 (d, 2H, J=9.0 Hz), 3.83 (s, 3H).

Preparation of compound RX-1810—Reaction of compound 26 with p-ethylaniline as above, preparation of compound RX-1805, followed by chromatography on SiO$_2$, gave compound RX-1810. $^1$H-NMR (300 MHz, CD$_3$OD): δ 8.75 (s, 1H), 8.55 (s, 1H), 8.44 (s, 1H), 7.95 (s, 1H), 7.60 (d, 2H, J=9.0 Hz), 7.00 (d, 2H, J=9.0 Hz), 2.70 (m, 2H), 1.27 (m, 2H).

Preparation of compound RX-1813—Reaction of compound 26 with 3-fluorophenethylaniline as above, preparation of compound RX-1805, followed by chromatography on SiO$_2$, gave compound RX-1813. $^1$H-NMR (300 MHz, CH$_3$OD): δ 8.43 (m, 3H), 7.88 (s, 1H), 7.38 (t, 1H, J=6.0 Hz), 7.07 (m, 2H), 6.89 (t, 1H, J=7.0 Hz), 3.89 (m, 2H), 3.07 (m, 2H).

Preparation of compound RX-1815—Reaction of compound 26 with aniline as above, preparation of compound RX-1805, followed by chromatography on SiO$_2$, gave compound RX-1815. $^1$H-NMR (300 MHz, CD$_3$OD): δ 8.76 (s, 1H), 8.53 (s, 1H), 8.45 (s, 1H), 7.96 (s, 1H), 7.75 (d, 2H, J=6.0 Hz), 7.42 (t, 2H, J=8.0 Hz), 7.21 (t, 1H, J=6.0 Hz).

Preparation of compound RX-1818—Reaction of compound 26 with 2,4,6-trifluoromethylaniline as above, preparation of compound RX-1805, followed by chromatography on SiO$_2$, gave compound RX-1818. $^1$H-NMR (300 MHz, CD$_3$OD): δ 8.56 (s, 1H), 8.37 (s, 1H), 8.16 (s, 1H), 7.75 (s, 1H), 7.00 (s, 2H), 2.34 (s, 3H), 2.21 (s, 6H).

Preparation of compound RX-1819—Reaction of compound 26 with 2-methylaniline as above, preparation of compound RX-1805, followed by chromatography on SiO$_2$, gave compound RX-1819. $^1$H-NMR (300 MHz, CD$_3$OD): δ 8.77 (s, 1H), 8.56 (s, 1H), 8.39 (s, 1H), 8.00 (s, 1H), 7.29 (m, 4H), 2.22 (s, 3H).

Preparation of compound RX-1828—Reaction of compound 26 with phenethylamine as above, preparation of compound RX-1805, followed by chromatography on SiO$_2$, gave compound RX-1828. $^1$H-NMR (300 MHz, CD$_3$OD): δ 8.46 (s, 1H), 8.41 (d, 2H, J=3.0 Hz), 7.89 (s, 1H), 7.27 (m, 5H), 3.87 (m, 2H), 3.08 (m, 2H).

Preparation of compound RX-1834—Reaction of compound 26 with isopropylamine as above, preparation of compound RX-1805, followed by chromatography on SiO$_2$, gave compound RX-1834. $^1$H-NMR (300 MHz, CD$_3$OD): δ 8.56 (s, 1H), 8.46 (s, 1H), 8.37 (s, 1H), 7.86 (s, 1H), 4.60 (m, 1H), 1.35 (s. 6H).

Preparation of compound RX-1835—Reaction of compound 26 with 4-methylphenethylamine as above, preparation of compound RX-1805, followed by chromatography on SiO$_2$, gave compound RX-1835. $^1$H-NMR (300 MHz, CD$_3$OD): δ 8.47 (s, 1H), 8.41 (s, 2H), 7.89 (s, 1H), 7.10 (m, 4H), 3.85 (m, 2H), 3.32 (m, 2H), 2.29 (s, 3H).

Preparation of compound RX-1840—Reaction of compound 26 with α-methylbenzylamine as above, preparation of compound RX-1805, followed by chromatography on SiO$_2$,.gave compound RX-1840. $^1$H-NMR (300 MHz, CD$_3$OD): δ 8.69 (s, 1H), 8.48 (s, 1H), 8.34 (s, 1H), 7.88 (s, 1H), 7.40 (m, 5H), 5.87 (m, 1H), 1.67 (m, 3H).

Preparation of compound RX-1842—Reaction of compound 26 with 4-phenylbutylamine as above, preparation of compound RX-1805, followed by chromatography on SiO$_2$, gave compound RX-1842. $^1$H-NMR (300 MHz, CD$_3$OD): δ 8.45 (d, 2H, J=3.0 Hz), 8.37 (s, 1H), 7.86 (s, 1H), 7.19 (m, 5H), 3.66 (m, 2H), 2.67 (m, 2H), 1.76 (m, 4H).

Example 6

1-Methyl-2,3-dihydro-1H-imidazo[4,5-g]guinazoline Compounds

Scheme 6

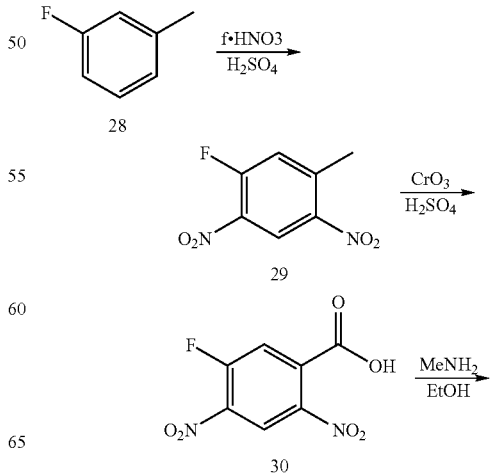

-continued

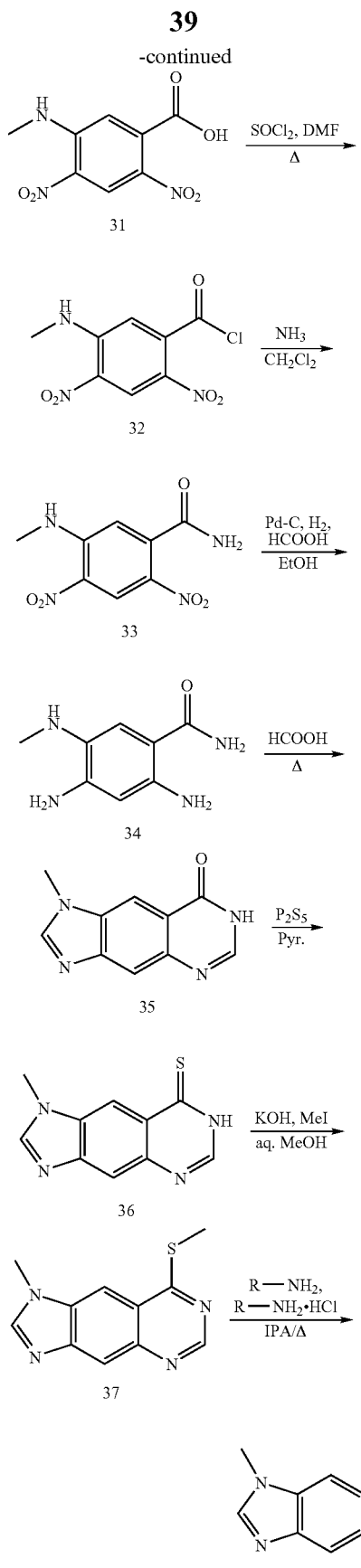

TABLE 11

![structure: 1-methyl-imidazo-quinazoline with HN-R at 4-position]

| Compd. No RX- | R |
|---|---|
| 1857 | —(CH$_2$)$_2$—(2-F-phenyl) |
| 1860 | —(4-CH$_2$CH$_3$-phenyl) |
| 1873 | —CH$_2$—(2,5-diF-phenyl) |
| 1881 | —CH$_2$—(3-F-phenyl) |
| 1892 | —(CH$_2$)$_4$—phenyl |
| 1894 | —(CH$_2$)$_2$—(3-F-phenyl) |
| 1895 | —phenyl |

Preparation of compound 29—Compound 28 (50 g, 0.45 mol) was added dropwise to a cooled solution of concentrated sulfuric acid (180 ml) and fuming nitric acid (125 ml) at 0° C. with stirring, and the mixture was stirred at room temperature for 30 min, before being cooled and poured onto ice-water. The resulting precipitate was collected, filtered, and dissolved in ethyl acetate. The organic solution was washed with saturated NaCl, dried over MgSO4, and evaporated under reduced pressure. The solid residue was recrystallized from CH$_2$Cl$_2$/Hexane to give compound 29 (63 g, 70%). $^1$H-NMR (300 MHz, CDCl$_3$): δ 8.23 (s, 1H), 7.35 (s, 1H), 2.76 (s, 3H).

Preparation of compound 30—To a cooled solution of compound 29 (29.5 g, 0.15 mol) dissolved in concentrated sulfuric acid (280 ml) was added dropwise CrO$_3$ (35.4 g, 2.4 eq, 0.35 mol) dissolved in water (25 ml) for 20 min. The mixture was stirred at room temperature for 4 hrs, and the product was extracted with ethyl acetate. The organic layer was washed with saturated NaHCO$_3$, dried over MgSO$_4$ and concentrated to give compound 30 (17.3 g, 50%). $^1$H NMR (300 MHz, CDCl$_3$): δ 8.59 (s, 1H), 7.61 (s, 1H).

Preparation of compound 31—To 15 g of compound 30 (65 mmol) dissolved in ethyl alcohol (100 ml) was added 30 ml of 40% aqueous methylamine. The precipitated solid was collected by filtration and washed with ethyl alcohol to give compound 31 (15.7 g, 86%). $^1$H-NMR (300 MHz, d$_6$-DMSO): δ 8.98 (s, 1H), 8.78 (s, 1H), 7.14 (s, 1H), 3.06 (s, 3H).

Preparation of compound 32—A solution of compound 31 (15 g, 62 mmol) in SOCl$_2$ (100 ml) containing, 2 drops of DMF was heated under reflux for 2 hrs. Excess SOCl$_2$ was removed under reduced pressure to give compound 32 (15.3 g, 95%).

Preparation of compound 33—To 15 g of;,compound 32 (57.7 mmol) in CH$_2$Cl$_2$ (100 ml) was added 43 ml of 2M ammonia in isopropyl alcohol (1.5 eq, 86.6 mmol) at 0° C. The mixture was stirred for 1 h and the solvent was removed under reduced pressure. The solid residue was recrystallized from EtOH/CH$_2$Cl$_2$ to give comxpound 33 (13.9 g, 85%). $^1$H-NMR (300 MHz, d$_6$-DMSO): δ 8.95 (s, 1H), 8.81 (s, 1H), 8.12 (s, 1H), 7.83 (s, 1H), 7.03 (s, 1H), 3.10 (s, 3H).

Preparation of compound 34—A suspension of compound 33 (13 g, 54 mmol) in ethyl alcohol (100 ml) containing formic acid (25 ml) was hydrogenated over 5% Pd/C (470 mg) at 30 psi and filtered, through Celite. Evaporation of the solvent gave comnpound 34 (9.7 g, 95%).

Preparation of compound 35—A solution of compound 34 (9 g, 50 mmol) in HCOOH (100 ml) was heated under reflux for 2 hrs. Excess HCOOH was removed under reduced pressure, and the residue was dissolved in 1N-HCl, filtered through Celite and basified with concentrated ammonia. The resulting solid was collected by filtration to give compound 35 (5 g, 50%). $^1$H-NMR (300 MHz, d$_6$-DMSO): δ 8.51 (s, 1H), 8.34 (s, 1H), 8.00 (s, 1H), 7.90 (s, 1H), 3.96 (s, 3H).

Preparation of compound 36—A mixture of compound 35 (2.5 g, 12.5 mmol) and 2 eq of phosphorous pentasulfide (5.55 g, 25 mmol) in dried pyridine (40 ml) was heated under reflux for 16 hrs, and the pyridine was removed under reduced pressure. The residue was treated with boiling water, and the resulting yellow precipitate was collected by filtration and dissolved in 0.1M KOH solution. After filtration to remove insolubles, the solution was neutralized with saturated NH$_4$Cl and the solvent was evaporated under reduced pressure to give compound 36 (1.1 g, 41%). $^1$H-NMR (300 MHz, d$_6$-DMSO): δ 8.92(s, 1H), 8.65 (s, 1H), 8.22 (s, 1H), 8.17 (s, 1H), 4.01 (s, 3H).

Preparahon of compound 37—To a solution of compound 36 (1 g, 4.6 mmol) and 1 N KOH (1.4 eq, 6.44 ml) in 50% MeOH/water (20 ml) was added dropwise MeI (0.7 g, 5.0 mmol) at 0° C., and the mixture was stirred at room temperature for 0.5~1 hr. The solution was neutralized with 1N HCl and the solvent was removed under reduced pressure. The crude residue was purified by SiO$_2$ column chromatography (silica gel; 230-400 mesh) to give compound 37 (0.26 g, 25%). $^1$H-NMR (300 MHz, d$_6$-DMSO): δ 8.93 (s, 1H), 8.67 (s, 1H), 8.23 (s, 1H), 8.21 (s, 1H), 4.01 (s, 3H), 2.74 (s, 3H).

Preparation of compound RX-1857—A mixture of compound 37 (20 mg, 0.087 mmol), 1.5 eq of 2-fluorophenylethylamine (17 ul, 0.131 mmol), and 1.5 eq of 2-fluorophenylethylamine hydrochloride (23 mg, 0.131 mmol) in isopropyl alcohol (20 ml) was heated under reflux for 8 hrs. After cooling the solvent was removed under reduced pressure. The resulting residue was purified by SiO$_2$ column chromatography (silica gel; 230-400 mesh) to give compound RX-1857 (8.4 mg, 30%). $^1$H-NMR (300 MHz, CD$_3$OD): δ 8.42 (s, 2H, J=3.0 Hz), 8.27 (s, 1H), 7.99 (s, 1H), 7.08 (m, 2H), 6.83 (m, 2H), 4.01 (s, 3H), 3.92 (m, 2H), 3.14 (m, 2H).

Preparation of compound RX-1860—Reaction of compound 37 with p-ethylaniline as above, preparation of compound RX-1857, followed by chromatography on SiO$_2$, gave compound RX-1860. $^1$H-NMR (300 MHz, CD$_3$OD): δ 8.96 (s, 1H), 8.58 (d, 2H, J=9.0 Hz), 7.96 (s, 1H), 7.61 (d, 2H, J=9.0 Hz), 7.21 (d, 2H, J=9.0 Hz), 4.01 (s, 3H), 2.59 (m, 2H), 1.17 (m, 3H).

Preparation of compound RX-1873—Reaction of compound 37 with 2,5-difluorobenzylamine as above, preparation of compound RX-1857, followed by chromatography on SiO$_2$, gave compound RX-1873. $^1$H-NMR (300 MHz, CD$_3$OD): δ 8.46 (m, 3H), 8.05 (s, 1H), 7.17 (m, 2H), 7.08 (s, 1H), 4.95 (s, 2H), 4.03 (s, 3H).

Preparation of compound RX-1881—Reaction of compound 37 with 3-fluorobenzylamine as above, preparation of compound RX-1857, followed by chromatography on SiO$_2$, gave compound RX-1881. $^1$H-NMR (300 MHz, CD$_3$OD): δ 8.39 (s, 2H), 8.30 (s, 1H), 7.98 (s, 1H), 7.28 (m, 3H), 7.06 (s, 1H), 4.91 (s, 2H), 3.99 (s, 3H).

Preparation of compound RX-1892—Reaction of compound 37 with 4-phenylbutylamine as above, preparation of compound RX-1857, followed by chromatography on SiO$_2$, gave compound RX-1892. $^1$H-NMR (300 MHz, CD$_3$OD): δ 8.43 (s, 1HHj, 8.38 (t, 2H, J=8.0 Hz), 7.99 (s, 1H), 7.22 (m, 5H), 4.00 (s, 3H), 3.75 (m, 2H), 2.92 (m. 2H), 2.68 (m, 4H).

Preparation of compound RX-1894—Reaction of compound 37 with 3-fluorophenethylamine as above, preparation of compound RX-1857, followed by chromatography on SiO$_2$, gave compound RX-1894. $^1$H-NMR (300 MHz, CD$_3$OD): δ 8.43 (s, 2H), 8.29 (s, 1H), 8.00 (s, 1H), 7.31 (m, 1H), 7.04 (m, 3H), 3.99 (s, 3H), 3.91 (m, 2H), 3.09 (m, 2H).

Preparation of compound RX-1895—Reaction of compound 37 with aniline as above, preparation of compound RX-1857, followed by chromatography on SiO$_2$, gave compound RX-1895. $^1$H-NMR (300 MHz, CD$_3$OD): δ 8.77 (s, 1H), 8.55 (d, 2H, J=3.0 Hz), 8.11 (s, 1H), 7.81 (d, 2H, J=9.0 Hz), 7.47 (m, 2H), 7.31 (t, 1H, J=7.0 Hz), 4.09 (s, 3H).

Example 7

Cell Growth Inhibition of Quinazoline Compounds

Growth of Cancer Cell Lines

Cancer cells used in this study to determine the effect of quinazoline compounds were obtained from the following sources: Human OVCAR-3 (ovary), MCF-7 (breast, hormone-dependent), Hs 578T (breast), MDA-MB-231 (breast), HeLa (cervix), PC3 (prostate), HepG2 (liver), A549 (lung), Caki-1 (kidney), HT-29 (colon), HCT116 (colon) and PANC-1 (pancreas) from the American Type Culture Collection (ATCC) (Manassas, Va.); U251 (brain) from Riken (Japan); MKN-45 (stomach) from DSMZ (Germany); UMRC2 (kidney) and Lox IMVI (melanoma) from the United States National Cancer Institute (Bethesda, Md.). All cell lines except Hs 578T, MDA-MB-231, HCT116, UMRC2, Caki-1 and PANC-1 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 μg/ml streptomycin ("P/S"). Hs 578T, MDA-MB-231, HCT116, UMRC2, Caki-1 and PANC-1 cells were maintained in Dulbecco's modified Eagle's medium ("DMEM", Invitrogen) supplemented with 10% FBS, P/S, 10 mM HEPES and 2 mM L-glutamine. All cells were incubated at 37° C. under humidified 5% $CO_2$.

Cell Growth Inhibition Assay

The growth inhibition of the substituted quinazoline derivative compounds against a variety of human tumor cells was evaluated. The relative importance of particular substituent groups on the compounds was also studied. The substituted quinazoline derivative compounds, prepared as described above, were tested, along with DMSO as a control.

The growth inhibition assay of various compounds against 15 human tumor cell lines was performed using the Sulforhodamnine B ("SRB") method (Skehan et al., J. National Cancer Institute, 82: 1107-1112 (1990)). Briefly, exponentially growing tumor cells were seeded into a 96-well plate at a density of 2-3×10³ cells/well and treated with quinazoline compounds the next day. Triplicate wells were used for each treatment. The cells were. incubated with the various compounds for 96 hours at 37° C. in a humidified 5% $CO_2$ atmosphere. After 96-hour incubation, cells were fixed with 10% trichloroacetic acid ("TCA"), incubated for 1 hour at 4° C., and washed 3 times with tap water. Subsequently cells were stained with 0.4% sulforhodamine B in 1% acetic acid for 30 minutes, washed 4 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.).

To translate the $OD_{530}$ values into the number of live cells in each well, the $OD_{530}$ values were compared to those on standard $OD_{530}$—versus—cell number curves generated for each cell line. The percent survival was calculated using the formula:

% Survival=live cell number [test]/live cell number [control]×100

The $IC_{50}$ values were calculated by non-linear regression analysis.

Using QSAR and combinatorial chemistry techniques, a large number of compounds, including the compounds shown in Tables 1-12 above, were synthesized. The synthesized compounds were screened against at least three cell lines, MCF-7, HepG2 and MKN-45, at approximately 1 μM concentration. Compounds showing activity in at least one of these cell lines were selected for further screening. The compounds listed in Tables 1-12 showed substantial activity for therapeutic use. From these compounds, thirty six were selected for further evaluation as broad spectrum anti-proliferative agents.

The inhibition of cell growth (IC50, μM) by the thirty six selected quinazoline compounds is shown in Tables 13 and 14 below:

TABLE 13

Inhibition of cell growth ($IC_{50}$, μM) by quinazoline compounds against human cancer cell lines

| Drug | A549 | HepG 2 | MKN-45 | PANC-1 | HT-29 | PC3 | HCT116 | U251 |
|---|---|---|---|---|---|---|---|---|
| RX-0183 | 1.13 | 0.25 | * | 0.091 | 0.95 | * | 0.33 | 0.47 |
| RX-1058 | 2.01 | 0.7 | 0.68 | * | * | * | | 1.93 |
| RX-1059 | * | 0.95 | 1.13 | 2.16 | * | * | | 2.50 |
| RX-1122 | 2.00 | 2.39 | 1.33 | 1.42 | 2.55 | 0.88 | | 0.57 |
| RX-1142 | 0.72 | 0.45 | 0.29 | 0.87 | 1.78 | 1.9 | | 0.73 |
| RX-1160 | * | 1.29 | * | 0.76 | * | * | | 1.96 |
| RX-1195 | 2.10 | 1.18 | * | 0.34 | 2.07 | * | | 1.95 |
| RX-1230 | * | 2.20 | * | * | * | * | | 0.60 |
| RX-1242 | 2.40 | 0.9 | * | * | * | * | | 0.56 |
| RX-1243 | * | 0.71 | * | 1.43 | * | * | | 0.61 |
| RX-1251 | 1.92 | 0.90 | * | * | * | * | | 0.42 |
| RX-1260 | * | 2.25 | * | * | * | * | | 0.69 |
| RX-1279 | 2.86 | 0.75 | * | * | * | * | | 2.97 |
| RX-1541 | 1.89 | 0.91 | * | 0.22 | 1.26 | * | | 1.78 |
| RX-1656 | * | 1.21 | * | * | * | * | | 0.46 |
| RX-1659 | * | 1.00 | * | * | * | * | | 0.51 |
| RX-1664 | * | 2.17 | * | * | * | * | | 0.71 |
| RX-1668 | * | 0.30 | * | 1.83 | * | * | | 0.27 |
| RX-1670 | * | 1.51 | * | * | * | * | | 0.62 |
| RX-1674 | * | 0.90 | * | * | * | * | | 0.36 |
| RX-1675 | * | 0.60 | * | * | * | * | | 0.30 |
| RX-1682 | * | 1.51 | * | * | * | * | | 0.53 |
| RX-1701 | * | 1.16 | * | * | * | * | | 2.19 |
| RX-1792 | 0.74 | 1.01 | 0.25 | 1.07 | 0.53 | 0.52 | | 0.35 |
| RX-1798 | 0.91 | 1.93 | 0.38 | 3.00 | 1.23 | 0.94 | | 0.56 |
| RX-1805 | * | 1.17 | * | * | * | * | | 1.81 |
| RX-1806 | * | 0.34 | * | * | * | * | | 1.33 |
| RX-1807 | * | 2.58 | * | * | * | * | | * |
| RX-1810 | * | 0.77 | * | * | * | * | | 2.56 |
| RX-1815 | * | 0.53 | * | * | * | * | | 2.23 |
| RX-1834 | 0.66 | 0.18 | 0.10 | * | 0.24 | 1.03 | | 0.13 |
| RX-1842 | * | 2.47 | * | * | * | * | | 1.93 |
| RX-1857 | * | * | * | * | * | * | | * |
| RX-1860 | * | 1.93 | * | * | * | * | | 2.24 |
| RX-1881 | * | 1.29 | * | * | * | * | | 0.91 |
| RX-1894 | * | 0.85 | * | * | 1.70 | * | | 0.90 |

*: >3.0 uM

TABLE 14

Inhibition of cell growth (IC$_{50}$, μM) by quinazoline compounds against human cancer cell lines

| Drug | HeLa | Lox IMVI | OVCAR-3 | MCF-7 | MDA-MB-231 | Hs 578T | UMRC2 | Caki-1 |
|---|---|---|---|---|---|---|---|---|
| RX-0183 | * | 1.62 | 2.46 | 0.33 | 0.13 | 0.035 | 0.11 | * |
| RX-1058 | 1.59 | * | 0.89 | 2.47 | 0.82 | 1.76 | 0.58 | 1.01 |
| RX-1059 | * | * | 1.18 | * | 0.73 | 1.51 | 1.20 | 0.83 |
| RX-1122 | 1.30 | 1.10 | 1.01 | 0.63 | 0.73 | 1.35 | 1.09 | 1.11 |
| RX-1142 | 0.87 | 2.53 | 0.37 | 0.80 | 0.14 | 0.44 | 0.32 | 0.45 |
| RX-1160 | * | * | * | 1.55 | 1.10 | 0.33 | 1.03 | * |
| RX-1195 | * | 2.16 | 2.60 | 1.53 | 0.46 | 0.44 | 0.41 | * |
| RX-1230 | * | 1.62 | * | 0.52 | 1.98 | 2.44 | * | 3.04 |
| RX-1242 | * | 0.73 | * | 0.58 | 0.88 | 1.03 | 1.29 | 2.39 |
| RX-1243 | * | * | * | 0.56 | 2.12 | 0.68 | 1.33 | 1.65 |
| RX-1251 | * | 0.19 | * | 0.55 | 0.34 | 0.43 | 0.47 | 1.96 |
| RX-1260 | * | * | * | 0.74 | * | * | * | * |
| RX-1279 | * | * | * | * | * | * | * | 2.15 |
| RX-1541 | * | 2.96 | 2.86 | 1.26 | 0.47 | 0.53 | 0.37 | * |
| RX-1656 | * | * | * | 0.36 | * | * | * | * |
| RX-1659 | * | 1.95 | * | 0.36 | * | * | * | 1.71 |
| RX-1664 | * | * | * | 0.68 | * | * | * | * |
| RX-1668 | * | * | * | 0.23 | * | 0.89 | 1.83 | 2.93 |
| RX-1670 | * | 0.88 | * | 0.43 | 1.06 | 1.35 | 1.53 | * |
| RX-1674 | * | * | * | 0.41 | * | * | * | * |
| RX-1675 | * | * | * | 0.24 | * | 1.35 | * | 2.61 |
| RX-1682 | * | * | * | 0.55 | * | * | * | * |
| RX-1701 | * | * | * | 1.36 | * | * | * | 2.85 |
| RX-1792 | 0.55 | 0.94 | 0.32 | 0.29 | 0.42 | 0.62 | 0.43 | 1.17 |
| RX-1798 | 1.37 | * | 0.85 | 0.53 | 0.72 | 2.00 | 0.92 | 2.95 |
| RX-1805 | * | * | * | 2.34 | 1.98 | * | * | 2.98 |
| RX-1806 | * | * | * | 1.19 | * | * | * | * |
| RX-1807 | * | * | * | * | * | * | * | * |
| RX-1810 | * | * | * | 1.75 | * | * | * | * |
| RX-1815 | * | * | * | 1.96 | * | * | * | 2.73 |
| RX-1834 | 1.06 | 0.67 | 0.48 | 0.11 | 0.53 | 0.79 | 2.24 | 0.65 |
| RX-1842 | * | 1.15 | * | 1.34 | 0.84 | 1.05 | 1.98 | * |
| RX-1857 | * | * | * | * | * | * | * | 1.57 |
| RX-1860 | * | * | 2.88 | 2.06 | * | * | * | 1.48 |
| RX-1881 | * | * | * | 0.68 | * | * | * | 2.34 |
| RX-1894 | * | * | * | 1.17 | * | * | * | 2.33 |

*: >3.0 uM

The compounds shown in Table 13 and 14 show activity against a broad range of tumor cell lines. Many of the compounds have activities, as determined by the IC$_{50}$ value, of significantly less than 2 μM or 2.5 μM, with several below 1.0 μM or even 0.5 μM. In particular, RX-0183 had an IC$_{50}$ of about 0.1 μM or less in three cell lines, PANC-1, Hs 578T and UMRC2 and significant activity in 9 other cell lines. The compound RX-1142 was significantly active in virtually all cell lines, with an IC$_{50}$<0.5 μM in 7 of the 15 cell lines assayed, with particularly high activity (IC$_{50}$=0.14 μM) toward MDA-MB-231. Activities of less than 1 μM were also observed for RX-1675. The compounds RX-1792 and RX-1834 exhibit broad activity at low concentrations, having an IC$_{50}$<1 μM in nearly all cell lines tested. The IC$_{50}$ of RX-1834 in particular was <0.2 μM in four of the tested cell lines. RX-1798 also showed a broad spectrum of activity, with an IC$_{50}$<2 μM for 11 of the 15 cell lines evaluated, and an IC$_{50}$<1 μM in 8 cell lines. As can be seen from Table 13 and 14, many of the other compounds tested exhibited IC$_{50}$<1 μM for a number of cell lines, with IC$_{50}$<0.5 μM in several. Values of IC$_{50}$ of less than or equal to 2.5 μM, 2.0 μM, 1.5 μM, 1.0 μM or 0.5 μM can reflect significant therapeutic activity. The IC$_{50}$ of the compounds of Table 13 and 14 thus reflect significant therapeutic activity.

Example 8

Ex Vivo Xenograft Study

In order to observe the inhibition of growth of tumor in an animal model, an ex vivo xenograft study of nude mice was conducted utilizing RX-0183. Suitable human cancer cell lines were those that have been tested already for inhibition of cancer cell growth, and particularly preferred was colon carcinoma HCT116. The antitumor efficacy of RX-0183 was evaluated against subcutaneously injected tumor xenografts in nude mice and tumor volume was measured after the treatment of RX-0183.

HCT116 cell suspension (2×10$^6$ cells in 0.1 ml of RPMI) was injected subcutaneously into the right flank of six-week-old male athymic mice (BALB/c nu/nu) on day 0. A sufficient number of mice were injected with HCT116 cell suspension so that tumors in a volume range as narrow as possible were selected for the trial on the day of treatment initiation. Tumors were allowed to reach 60-65 mm$^3$ in size before the start of treatment with RX-0183 on day 10. Animals with tumors in the proper size range were assigned to various treatment groups. RX-0183 was dissolved in 10% DMSO in PBS and solvent alone served as control. All study medications (control, RX-0183 1 mg/kg/day, RX-0183 3 mg/kg/day) were given by intraperitoneal injections three times per week starting from day 10 and ending on day 35.

To quantify tumor growth, three perpendicular diameters of the tumors were measured with calipers every 3-5 days, and the body weight of the mice was monitored for toxicity. The tumor volume was calculated using the formula: tumor volume (mm$^3$)=(width)×(length)×(height)×π/6.

Tumor volume (mean±SEM) in each group of animals is presented in FIG. 1, which shows a measurement of tumor volume as an indicator of efficacy of RX-0183 against HCT116 human colon carcinoma xenografts. The RX-0183 treatment was well tolerated without deaths and no more than 1 g body weight fluctuations was observed. After day 35, the tumor volume was significantly reduced in the mice treated with RX-0183 at 1 and 3 mg/kg treatment compared to the controls.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for treating tumors comprising administering a composition comprising a compound of the formula:

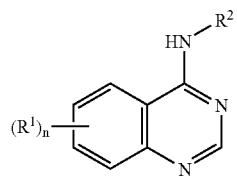

wherein:
n=1 or 2;
when n=1, $(R^1)_1$ is selected from 6-NHCH$_2$R$^3$, H, 6-nitro, 6-bromo, 6-iodo, 7-fluoro, and 5-methyl;
when n=2, $(R^1)_2$ is selected from 6,7-dimethoxy, 6,7-diethoxy, and imidazol[4,5-g]-; and
wherein R$^3$ is selected from the group consisting of —CH(CH$_3$)$_2$, and Ar, where Ar is selected from
(a) 4-substituted phenyl, wherein the 4-substituent is selected from —CH(CH$_3$)$_2$, —OCH$_2$Ph, —OCH$_2$CH$_2$CH$_3$, and -Ph;
(b) 3-substituted phenyl, wherein the 3-substituent is selected from methoxy, 4-chlorophenoxy, benzyloxy, 4-methoxyphenoxy, 4-methylphenoxy, 3-trifluoromethylphenoxy and methyl;
(c) 2-substituted phenyl, wherein the 2-substituent is selected from methyl, nitro, and benzyloxy;
(d) disubstituted phenyl selected from 2,4-dimethoxyphenyl, 2,6-dimethoxyphenyl, 2,5-dimethoxyphenyl, 3,5-dimethoxyphenyl, 2,5-dimethylphenyl, and 4,4-ethylenedioxy;
(e) pyridine-3-yl; and
(f) naphthylen-1-yl, optionally substituted with methoxy in the 2-position;
and
(i) when $(R^1)_1$ is 6-NHCH$_2$R$_3$, then R$^2$ is selected from 3-bromophenyl, 3-chloro-4-fluorphenyl, and (ii) when $(R^1)_1$ is H, 6-nitro, 6-bromo, 6-iodo, 7-fluoro, or 5-methyl, then R$^2$ is selected from
(a) cyclohexyl;
(b) a substituted phenyl, selected from 2,4,6-trimethylphenyl, 2-fluoro-4-chlorophenyl, 4-fluorophenyl, and 2-chlorophenyl;
(c) CH$_2$Ar, wherein Ar is selected from naphthylen-1-yl; 2-trifluoromethylphenyl, and 3-trifluoromethylphenyl;
(d) (CH$_2$)$_2$Ar, wherein Ar is selected from phenyl, 3-fluorophenyl, and 4-fluorophenyl;
(e) α-methylbenzyl; and
(f) 4-phenylbutyl;
(iii) when $(R^1)_2$ is 6,7-dimethoxy, then R$^2$ is selected from
(a) (CH$_2$)$_m$Ar, wherein, m is 1, 2 or 4 and, when m=1, Ar is selected from 2-chlorophenyl, 4-chlorophenyl, 2-fluorophenyl, 2-chloro-6-fluorophenyl, and 3-trifluoromethylphenyl; when m=2 then Ar is selected from phenyl and 3-fluorophenyl and when m=4, Ar is phenyl; and
(b) α-methylbenzyl;
(iv) when $(R^1)_2$ is 6,7-diethoxy, then R$^2$ is selected from
(a) (CH$_2$)$_m$Ar, wherein, m is 1, 2 or 4 and, when m=1, Ar is selected from 2-chlorophenyl, 4-chlorophenyl, 2-fluorophenyl, 2-chloro-6-fluorophenyl, 3-trifluoromethylphenyl, and 3,5-dimethoxyphenyl; when m=2 then Ar is selected from phenyl and 3-fluorophenyl and when m=4, Ar is phenyl; and
(b) α-methylbenzyl; and
(v) when $(R^1)_2$ is imidazol[4,5-g]-, then R$^2$ is selected from
(a) isopropyl;
(b) phenyl, optionally substituted in the 2-position with a methyl group or in the 4-position with a substituent selected from methoxy, ethyl, isopropyl, and n-butyl;
(c) 2,4,6,-trimethyl phenyl;
(d) CH$_2$Ar, wherein Ar is selected from 3-fluorophenyl and 2,5-difluorophenyl;
(e) (CH$_2$)$_m$Ar, wherein m is 2 or 4 and, when m=2, Ar is selected from phenyl, 3-fluorophenyl, 4-methylphenyl and when m=4, Ar is phenyl; and
(f) α-methylbenzyl or a pharmaceutically acceptable salt thereof to a subject in need of such treatment, thereby treating the tumor.

2. The method of claim 1, wherein the compound is selected from the group of compounds wherein
(A) R$^2$ is 3-chloro-4-fluorophenyl and $(R^1)_1$ is 6-NHCH$_2$R$^3$, wherein R$_3$ is selected from 4-isopropylphenyl and 2,4-dimethoxyphenyl;
(B) R$^2$ is 3-bromophenyl and $(R^1)_1$ is 6-NHCH$_2$R$^3$, wherein R$^3$ is 2-methylphenyl;
(C) $(R^1)_1$ is 6-bromo or 6-iodo and R$^2$ is selected from 2-(3-fluorophenyl)ethyl, 4-phenylbutyl, 2-phenylethyl, naphthylen-1-ylmethyl, 2-trifluoromethylphenylmethyl and 2-fluoro-4-chlorophenyl;
(D) $(R^1)_1$ is 6-nitro and R$^2$ is 2,4,6-trimethylphenyl;
(E) $(R^1)_1$ is H and R$^2$ is selected from 2-(3-fluorophenyl)ethyl, α-methylbenzyl, and 4-phenylbutyl;
(F) $(R^1)_1$ is 5-methyl and R$^2$ is 2-(4-fluorophenyl)ethyl;
(G) $(R^1)_1$ is 6-iodo and R$^2$ is selected from 3-trifluoromethylphenylmethyl, cyclohexyl and 2-chlorophenyl;
(H) $(R^1)_2$ is 6,7-diethoxy and R$^2$ is selected from 2-chlorophenylmethyl and 2-chloro-6-fluorophenylmethyl; and
(I) $(R^1)_2$ is imidazol[4,5-g] and R$^2$ is isopropyl, 4-phenylbutyl or phenyl that is optionally substituted in the 4-position with a substituent selected from hydrogen, butyl, isopropyl, ethyl, and methoxy or a pharmaceutically acceptable salt thereof.

3. The method of claim 1, wherein the compound is selected from the group of compounds wherein:

(A) $R^2$ is 3-chloro-4-fluorophenyl or 3-bromophenyl and $(R^1)_1$ is 6-NHCH$_2$R$^3$, wherein R$^3$ is selected from 4-isopropylphenyl, 2-methylphenyl and 2,4-dimethoxyphenyl;

(B) $(R^1)_1$ is H, 6-nitro, 6-bromo, 6-iodo, 7-fluoro, or 5-methyl and R$^2$ is selected from 2-(3-fluorophenyl)ethyl, 4-phenylbutyl, 2-phenylethyl, naphthylen-1-ylmethyl, 2-trifluoromethylphenylmethyl, 2-(4-fluorophenyl)ethyl, 2-fluoro-4-chlorophenyl, 3-trifluoromethylphenylmethyl, cyclohexyl, 2-chlorophenyl, 2,4,6-trimethylphenyl, α-methylbenzyl, and 4-phenylbutyl;

(C) $(R^1)_2$ is 6,7-dimethoxy or 6,7-diethoxy and R$^2$ is selected from 2-chlorophenylmethyl and 2-chloro-6-fluorophenylmethyl;

(D) $(R^1)_2$ is imidazol[4,5-g] and R$^2$ is selected from isopropyl, 4-phenylbutyl, 3-fluorophenylmethyl, 2-(2-fluorophenyl)ethyl, 2-(3-fluorophenyl)ethyl or phenyl that is optionally substituted in the 4-position with a substituent selected from hydrogen, butyl, isopropyl, ethyl, and methoxy or a pharmaceutically acceptable salt thereof.

4. The method of claim 1, wherein the compound is selected from the group of compounds wherein:

(A) R$^2$ is 3-chloro-4-fluorophenyl and $(R^1)_1$ is 6-NHCH$_2$R$^3$, wherein R$^3$ is 2-methylphenyl;

(B) $(R^1)_1$ is H and R$^2$ is 4-phenylbutyl;

(C) $(R^1)_1$ is 6-iodo and R$^2$ is 2-phenylethyl;

(D) $(R^1)_2$ is 6,7-diethoxy and R$^2$ is selected from 2-chlorophenylmethyl and 2-chloro-6-fluorophenylmethyl; and (E) $(R^1)_2$ is imidazol[4,5-g] and R$^2$ is isopropyl or a pharmaceutically acceptable salt thereof.

5. The method of claim 1, wherein the compound is

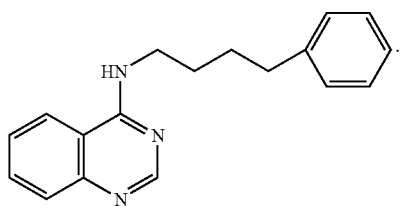

or a pharmaceutically acceptable salt thereof.

6. The method of claim 1, said composition further comprising a pharmaceutically acceptable carrier or diluent.

7. The method of claim 1, said tumor selected from tumors of the ovary, hormone-dependant tumors of the ovary, tumors of the breast, cervical tumors, tumors of the prostate, tumors of the liver, lung tumors, kidney tumors, colon tumors, pancreatic tumors, brain tumors, stomach tumors and melanoma.

8. A compound of the formula:

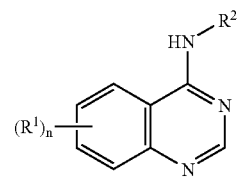

wherein:
n=1 or 2;
when n=1, $(R^1)_1$ is selected from 6-NHCH$_2$R$^3$, H, 6-nitro, 6-bromo, 6-iodo, 7-fluoro, and 5-methyl;
when n=2, $(R^1)_2$ is selected from 6,7-dimethoxy, 6,7-diethoxy, and imidazol[4,5-g]-; and
wherein R$^3$ is selected from the group consisting of —CH(CH$_3$)$_2$, and Ar, where Ar is selected from (a) 4-substituted phenyl, wherein the 4-substituent is selected from —CH(CH$_3$)$_2$, —OCH$_2$Ph, —OCH$_2$CH$_2$CH$_3$, and -Ph;

(b) 3-substituted phenyl, wherein the 3-substituent is selected from methoxy, 4-chlorophenoxy, benzyloxy, 4-methoxyphenoxy, 4-methylphenoxy, 3-trifluoromethylphenoxy and methyl;

(c) 2-substituted phenyl, wherein the 2-substituent is selected from methyl, nitro, and benzyloxy;

(d) disubstituted phenyl selected from 2,4-dimethoxyphenyl, 2,6-dimethoxyphenyl, 2,5-dimethoxyphenyl, 3,5-dimethoxyphenyl, 2,5-dimethylphenyl, and 4,4-ethylenedioxy;

(e) pyridine-3-yl; and (f) naphthylen-1-yl, optionally substituted with methoxy in the 2-position; and (i) when $(R^1)_1$ is 6-NHCH$_2$R$^3$, then R$^2$ is selected from 3-bromophenyl, 3-chloro-4-fluorphenyl, and (ii) when $(R^1)_1$ is H, 6-nitro, 6-bromo, 6-iodo, 7-fluoro, or 5-methyl, then R$^2$ is selected from (a) cyclohexyl;

(b) a substituted phenyl, selected from 2,4,6-trimethylphenyl, 2-fluoro-4-chlorophenyl, 4-fluorophenyl, and 2-chlorophenyl;

(c) CH$_2$Ar, wherein Ar is selected from naphthylen-1-yl; 2-trifluoromethylphenyl, and 3-trifluoromethylphenyl;

(d) (CH$_2$)$_2$Ar, wherein Ar is selected from phenyl, 3-fluorophenyl, and 4-fluorophenyl;

(e) α-methylbenzyl; and (f) 4-phenylbutyl;

(iii) when $(R^1)_2$ is 6,7-dimethoxy, then R$^2$ is selected from (a) (CH$_2$)$_m$Ar, wherein, m is 1, 2 or 4 and, when m=1, Ar is selected from 2-chlorophenyl, 4-chlorophenyl, 2-fluorophenyl, 2-chloro-6-fluorophenyl, and 3-trifluoromethylphenyl; when m=2 then Ar is selected from phenyl and 3-fluorophenyl and when m=4, Ar is phenyl; and (b) α-methylbenzyl;

(iv) when $(R^1)_2$ is 6,7-diethoxy, then R$^2$ is selected from (a) (CH$_2$)$_m$Ar, wherein, m is 1, 2 or 4 and, when m=1, Ar is selected from 2-chlorophenyl, 4-chlorophenyl, 2-fluorophenyl, 2-chloro-6-fluorophenyl, 3-trifluoromethylphenyl, and 3,5-dimethoxyphenyl; when m=2 then Ar is selected from phenyl and 3-fluorophenyl and when m=4, Ar is phenyl; and (b) α-methylbenzyl; and (v) when $(R^1)_2$ is imidazol[4,5-g]-, then $R^2$ is selected from
  (a) isopropyl;
  (b) phenyl, optionally substituted in the 2-position with a methyl group or in the 4-position with a substituent selected from methoxy, ethyl, isopropyl, and n-butyl;
  (c) 2,4,6,-trimethyl phenyl;
  (d) $CH_2Ar$, wherein Ar is selected from 3-fluorophenyl and 2,5-difluorophenyl;
  (e) $(CH_2)_mAr$, wherein m is 2 or 4 and, when m=2, Ar is selected from phenyl, 3-fluorophenyl, 4-methylphenyl and when m=4, Ar is phenyl; and
  (f) α-methylbenzyl
or a pharmaceutically acceptable salt thereof,
with the proviso that
  (a) when $R^2$ is $(CH_2)_2Ph$ or benzyl, $(R^1)_1$ is not H, 6-nitro, 6-bromo, or 6-iodo;
  (b) when $(R^1)_1$ is H, $R^2$ is not $(CH_2)_4Ph$, α-methylbenzyl or 2-chlorophenyl;
  (c) when $(R^1)_1$ is Br, $R^2$ is not α-methylbenzyl; and
  (d) when $(R^1)_2$ is 6,7-dimethoxy and $R^2$ is $(CH_2)_mAr$, then
    (i) when m=1, Ar is not 2-chlorophenyl or 3-trifluoromethylphenyl; and
    (ii) When m=2, Ar is not phenyl; and
  (e) when $(R^1)_2$ is 6,7-dimethoxy, $R^2$ is not α-methylbenzyl.

9. The compound of claim 8, selected from the group having:
  (A) $R^2$=3-chloro-4-fluorophenyl and $(R^1)_1$=6-$NHCH_2R^3$, wherein $R^3$ is selected from 4-isopropylphenyl and 2,4-dimethoxyphenyl;
  (B) $R^2$=3-bromophenyl and $(R^1)_1$=6-$NHCH_2R^3$, wherein $R^3$ is 2-methylphenyl;
  (C) $(R^1)_1$=6-bromo or 6-iodo and $R^2$ selected from 2-(3-fluorophenyl)ethyl, 4-phenylbutyl, naphthylen-1-ylmethyl, 2-trifluoromethylphenylmethyl and 2-fluoro-4-chlorophenyl;
  (D) $(R^1)_1$=6-nitro and $R^2$=2,4,6-trimethylphenyl;
  (E) $(R^1)_1$=H and $R^2$=2-(3-fluorophenyl)ethyl;
  (F) $(R^1)_1$=5-methyl and $R^2$=2-(4-fluorophenyl)ethyl;
  (G) $(R^1)_1$=6-iodo and $R^2$ selected from 3-trifluoromethylphenylmethyl, cyclohexyl and 2-chlorophenyl;
  (H) $(R^1)_2$=6,7-diethoxy and $R^2$ selected from 2-chlorophenylmethyl and 2-chloro-6-fluorophenylmethyl; and
  (I) $(R^1)_2$=imidazol[4,5-g] and $R^2$ selected from isopropyl, 4-phenylbutyl or phenyl that is optionally substituted in the 4-position with a substituent selected from butyl, isopropyl, ethyl, and methoxy or a pharmaceuticaly acceptable salt thereof.

10. The compound of claim 8 selected from the group having:
  (A) $R^2$=3-chloro-4-fluorophenyl or 3-bromophenyl and $(R^1)_1$=6-$NHCH_2R^3$, wherein $R^3$ is selected from 4-isopropylphenyl, 2-methylphenyl and 2,4-dimethoxyphenyl;
  (B) $(R^1)_1$=H, 6-nitro, 6-bromo, 6-iodo, 7-fluoro, or 5-methyl and $R^2$ selected from 2-(3-fluorophenyl)ethyl, 4-phenylbutyl, naphthylen-1-ylmethyl, 2-trifluoromethylphenylmethyl, 2-(4-fluorophenyl)ethyl, 2-fluoro-4-chlorophenyl, 3-trifluoromethylphenylmethyl, cyclohexyl, 2-chlorophenyl, 2,4,6-trimethylphenyl, and 4-phenylbutyl;
  (C) $(R^1)_2$=6,7-dimethoxy or 6,7-diethoxy and $R^2$ selected from 2-chlorophenylmethyl and 2-chloro-6-fluorophenylmethyl;
  (D) $(R^1)_2$=imidazol[4,5-g] and $R^2$ selected from isopropyl, 4-phenylbutyl, 3-fluorophenylmethyl, 2-(2-fluorophenyl)ethyl, 2-(3-fluorophenyl)ethyl or phenyl that is optionally substituted in the 4-position with a substituent selected from hydrogen, butyl, isopropyl, ethyl, and methoxy or a pharmaceutically acceptable salt thereof.

11. The compound of claim 8 selected from the group having:
  (A) $R^2$=3-chloro-4-fluorophenyl and $(R^1)_1$=6-$NHCH_2R^3$, wherein $R^3$=2-methylphenyl;
  (B) $(R^1)_2$=6,7-diethoxy and $R^2$ selected from 2-chlorophenylmethyl and 2-chloro-6-fluorophenylmethyl; and
  (C) $(R^1)_2$=imidazol[4,5-g] and $R^2$=isopropyl or a pharmaceutically acceptable salt thereof.

12. A pharmaceutical composition comprising a therapeutically effective amount of a compound of claim 8 and a pharmaceutically acceptable carrier or diluent.

13. The compound or salt of claim 8 having an $IC_{50}$ of not greater than 10 µM as determined by the SRB method with respect to at least one cell line for a tumor selected from tumors of the ovary, tumors of the breast, cervical tumors, tumors of the prostate, tumors of the liver, lung tumors, kidney tumors, colon tumors, pancreatic tumors, brain tumors, stomach tumors and melanoma.

14. The compound or salt of claim 13, wherein said cell line is selected from Human OVCAR-3 for tumors of the ovary; MCF-7, Hs 578T and MDA-MB-231 for tumors of the breast; HeLa for cervical tumors; PC3 for tumors of the prostate; HepG2 for tumors of the liver; A549 for lung tumors; Caki-1 or UMRC2 for kidney tumors; HT-29 and HCT116 colon tumors; PANC-1 for pancreatic tumors; U251 for brain tumors; MKN-45 for stomach tumors; and Lox IMVI for melanoma.

15. The compound or salt of claim 13 having an $IC_{50}$ of not greater than 1.0 µM as determined by the SRB method.

16. The compound or salt of claim 13 having an $IC_{50}$ of not greater than 0.5 µM as determined by the SRB method.

17. The compound

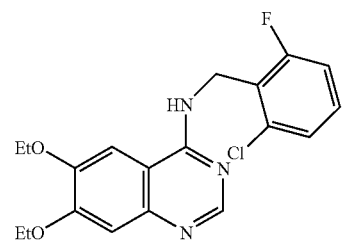

or a pharmaceutically acceptable salt thereof.

18. A method for treating tumors comprising administering a composition comprising a compound according to claim 17 or a pharmaceutically acceptable salt thereof.

19. The method of claim 1, wherein:
  n=2;
  $(R^1)_2$ is imidazol[4,5-g]-, and
  $R^2$ is isopropyl;
or a pharmaceutically acceptable salt thereof.

* * * * *